(12) United States Patent
Turnlund et al.

(10) Patent No.: US 9,078,784 B2
(45) Date of Patent: Jul. 14, 2015

(54) FLEXIBLE STRUCTURAL APPARATUS, SPRING, WOUND COVERING, AND METHODS

(75) Inventors: Todd H. Turnlund, Park City, UT (US); Ted W. Layman, Park City, UT (US); Richard A. Glenn, Santa Rosa, CA (US)

(73) Assignee: THT CONSULTING, LLC, Park City, UT (US)

( * ) Notice: Subject to any disclaimer, the term of this patent is extended or adjusted under 35 U.S.C. 154(b) by 733 days.

(21) Appl. No.: 12/701,333

(22) Filed: Feb. 5, 2010

(65) Prior Publication Data

US 2010/0198128 A1 Aug. 5, 2010

Related U.S. Application Data

(60) Provisional application No. 61/150,204, filed on Feb. 5, 2009.

(51) Int. Cl.
*A61F 13/00* (2006.01)
*A61F 15/00* (2006.01)

(52) U.S. Cl.
CPC .................... *A61F 15/008* (2013.01)

(58) Field of Classification Search
USPC ............ 602/60, 54, 42, 41, 55; 128/888, 846, 128/889; 606/215; 604/304, 307, 192–198; 2/455; D24/189
See application file for complete search history.

(56) References Cited

U.S. PATENT DOCUMENTS

| | | | |
|---|---|---|---|
| 2,520,436 A * | 8/1950 | Russell | 128/888 |
| 5,106,362 A | 4/1992 | Gilman | |
| 5,557,804 A * | 9/1996 | Ovortrup et al. | 2/23 |
| 6,641,527 B2 | 11/2003 | Khouri | |
| 2003/0109816 A1 | 6/2003 | Lachenbruch et al. | |
| 2004/0127836 A1 | 7/2004 | Sigurjonsson et al. | |
| 2005/0277860 A1 | 12/2005 | Jensen | |
| 2007/0106394 A1 | 5/2007 | Chen | |

OTHER PUBLICATIONS

International Search Report for PCT/US2010/023362, 8 pages. Jan. 7, 2011.

* cited by examiner

*Primary Examiner* — Victoria J Hicks
(74) *Attorney, Agent, or Firm* — Allan W. Watts; Bryan Cave LLP

(57) ABSTRACT

A flexible structural apparatus which may be used as a wound covering which extends above the wound such that the wound covering does not contact the wound and also protects the wound from contact. The apparatus provides a high degree of flexibility while retaining structural strength and resisting collapse, for example, so as to adequately protect the wound. Various embodiments include parallel beams and connections between beams that alternate in location along the beams to provide flexibility. Some embodiments may be used as springs and may have attachment features, such as holes, which may be located at the end beams, for example.

20 Claims, 27 Drawing Sheets

FLEXIBLE STRUCTURAL APPARATUS, SPRING, WOUND COVERING, AND METHODS

RELATED PATENT APPLICATIONS

This patent application claims priority to U.S. Provisional Patent Application No. 61/150,204, filed on Feb. 5, 2009, having the same title and inventors, the contents of which are incorporated herein by reference.

FIELD OF THE INVENTION

The present invention relates to flexible structures and springs and methods of making and using such devices. Particular embodiments concern wound coverings, including raised wound coverings that protect the wound from contact, enclose the wound, or both.

BACKGROUND OF THE INVENTION

Various structures have been invented and used for many different purposes. In particular applications, flexure of structures has been taken into consideration and designs have been invented or selected to allow a structure to flex as needed in the particular application at hand. Needs and potential for benefit exist, however, for new and improved structures that provide a beneficial measure of stiffness while providing better flexibility, at least in certain dimensions. In addition, many different shapes and sizes of springs have been used for many different purposes. Needs and potential for benefit exist, however, for springs having new shapes that may fit better into particular available spaces, that may have different force-displacement characteristics, and that may have other unique characteristics that may prove to be advantageous in certain applications. Thus, the potential for advancement in the areas of flexible structures and springs have not been exhausted. Needs and potential for benefit also exist for flexible structures and springs that are inexpensive or easy to manufacture, easy to use, are reliable, and provide the benefits desired in particular applications.

In a particular area of technology, bandages have been used to protect wounds. Wounds or damage to the skin or other tissue occur quite frequently and most people experience various different wounds during their lives. Wounds, as the term is used herein, may occur accidentally or may be the result of a surgery, as examples. While many wounds may heal relatively easily, many types of wounds such as scrapes, burns, skin grafts, etc., as examples, are sensitive to subsequent damage. In order to heal, many wounds need protection from foreign matter such as dirt or bacteria, but may also benefit from protection from physical contact. Disturbing such a wound may cause pain, increase healing time, cause additional scarring or damage, worsen the patient's health, or a combination thereof, as examples. In may instances it is desirable to protect a wound from further damage in the area of the wound.

Bandages have been used to protect wounds from foreign material, and, to some extent, from impacts, but bandages typically have not been very effective at protecting wounds from forces perpendicular to the skin or tissue. Casts have been used to immobilize limbs when bones have been broken, for example, and casts are resistant to generally perpendicular forces, but casts generally do not allow the limbs or tissue to move. In addition, it is often desirable to keep the bandage or wound covering from touching the wound. Often, the covering will stick to the wound if it touches the wound, causing damage to the wound if the covering is removed or even when the wound moves as the person moves their body. In some applications, it is desirable that a wound covering allow for unrestricted or less-restricted motion of the wound. Wounds frequently occur on joints or areas of the body where the skin moves, stretches, or shifts significantly when the person makes ordinary movements such as walking, eating, etc. Treating wounds on joints is thus difficult because joints require complex motion. In order to allow movement of a joint, a wound covering placed on the joint must often allow simultaneous bending, stretching, and twisting, as examples.

Wounds are often treated by placing ointment or medication on the wound and then placing a bandage on the wound. The bandage typically contacts the wound. Having the bandage contact the wound is often undesirable as the bandage may stick to the wound, causing damage to the wound when the bandage is removed or when the wound moves due to the person moving. Additionally, a bandage which contacts the wound may cause pain or further damage to a sensitive wound such as a burn, or may irritate the wound, possibly causing increased inflammation or causing the person to scratch at the wound, as examples. Conventional bandages do little to prevent accidental contact with the bandage from pressing against the wound. Thus, a bandage which contacts the wound may cause further damage or an increased level of discomfort.

Various attempts have been made to provide a wound covering which is elevated above a wound so that the covering does not touch the wound. For example, a covering has been designed which uses a foam square around the perimeter of the wound covering with a sheet of covering material attached thereto. The foam square keeps the covering material elevated off of the wound. The foam bends fairly easily in one direction perpendicular to the wound covering, but thereafter may not be able to bend in another direction to form a compound curve. The wound covering also may not be able to easily stretch or change shape within the plane of the wound covering because the sheet of covering material essentially forms a shear web.

Another wound covering uses a domed plastic cover with a corrugated section formed across the center thereof to provide flexibility. This type of design, however, has several limitations. Larger corrugations provide increased flexibility but increase the bulkiness of the wound covering, either increasing the overall height of the covering or reducing the distance between the covering and the wound. Smaller corrugations are less flexible. A stronger material of construction increases the resistance of the wound covering to collapse, but reduces the flexibility. Softer materials provide improved flexibility, but reduce the strength of the covering and allow it to more easily collapse against the wound. These corrugated wound coverings provide some flexibility for bending at the corrugated joint in a lateral or vertical direction, but allow for little twisting, stretching, or skewing of the shape. Thus, they do not provide adequate flexibility for use on many locations of the body.

Therefore, there is need for or potential for benefit from a strong, flexible, low profile wound covering. There is also a need for or potential for benefit from a wound covering which prevents contact with the wound. Further, there is also a need for or potential for benefit from a wound covering which is sufficiently strong to prevent collapse thereof, but which is capable of easily bending, stretching, twisting, and skewing so as to accommodate the similar movements of the skin when a person moves.

There are also needs for and potential for benefit from other structures which are flexible. Specifically, there are also needs for and potential for benefit from other structures that are stiff when loads are applied in one direction and yet are flexible in other directions, for example, when supports or a supporting surface for the structure moves relative to other supports or portions of the supporting surface. Such flexible structures may be used as springs, for example. Other needs and potential for benefit may be apparent to a person of skill in the art of structural design.

SUMMARY OF PARTICULAR EMBODIMENTS OF THE INVENTION

Various embodiments of the invention provide, for example, as an object or benefit, that they partially or fully address or satisfy one or more of the needs, potential areas for benefit, or opportunities for improvement described herein, or known in the art, as examples. Some embodiments of the invention provide a flexible wound covering, for example. In some embodiments, for instance, a flexible (e.g., domed) structure flexes with body movement, but presents a barrier which prevents objects from pressing against or exerting a force against the wound. In particular embodiments, for example, the domed structure comprises interconnected individual structural members. The individual structural members may collectively provide strength and resistance to collapse, but may also be interconnected in such a way that the wound covering provides good flexibility and accommodates some stretching and complex movement, for example. These and other aspects of the present invention may be realized in whole or in part in various wound covering devices as shown, described, or both in the figures and related description herein. Besides wound covering devices, some embodiments may be used for other purposes, such as for other flexible structures or as springs, as examples. Other uses and applications are described herein or may be apparent to a person of skill in the art.

In specific embodiments, the invention provides various flexible structural apparatus that may include, for example, multiple beams and multiple connections between the beams. A number of embodiments may include multiple substantially parallel beams that may include, for example, two end beams and multiple intermediate beams. The intermediate beams may be in between the two end beams, and each beam may have a length, a width, and a height. In certain embodiments, for multiple of the beams, the length may be at least four times greater than the width and the length may be at least four times greater than the height. In a number of embodiments, each connection connects one of the beams to one other of the beams, and each beam may have at least one connection to at least one other beam and each intermediate beam may have multiple connections to at least two other beams. In various embodiments, each connection may have a width dimension parallel to the length of the beams, and the width dimension of the connection may be no greater than one fourth of the length of either of the beams that the connection is between. Further, in many embodiments, each intermediate beam is restrained relative to other beams only at the connections.

Further, in a number of embodiments, the multiple connections may include, for example, multiple first connections and multiple second connections and multiple intermediate beams may each have at least one first connection to a first adjacent beam and at least one second connection to a second adjacent beam, for instance. In many embodiments, for each of the multiple intermediate beams, the at least one first connection and the at least one second connection may be spaced apart along the length of the beam by a distance of at least one fourth of the length of the beam with no other connections therebetween. Moreover, in a number of embodiments, from one end beam to the other end beam, the connections may alternate between the at least one first connection and the at least one second connection.

In particular embodiments, intermediate beams may each have at least two first connections to a first adjacent beam and at least one second connection to a second adjacent beam. In some such embodiments, for each of the multiple intermediate beams, each of the at least two first connections and the at least one second connection may be spaced apart along the length of the beam by a distance between connections of at least one fourth of the length of the beam. Furthermore, in some embodiments, for each of the multiple intermediate beams, one of the first connections may be located along the length of the beam within a distance of no more than one fifth of the length of the beam from a first end of the beam and one of the first connections may be located along the length of the beam within a distance of no more than one fifth of the length of the beam from a second end of the beam.

In certain embodiments, each beam has a midpoint, and for each of the multiple intermediate beams, at least one second connection may be located along the length of the beam within a distance of no more than one fifth of the length of the beam from the midpoint. Further, in some embodiments, multiple of the intermediate beams may each have a preformed camber in a direction of the height of the beam. In particular embodiments, different intermediate beams may have a different amount of camber in the direction of the height of the beam, and the amount of camber may vary from beam to beam from a lesser amount of camber near the end beams to a greater amount of camber midway between the end beams. Further still, in some embodiments, different intermediate beams may have a different length, and the lengths of the beams may vary from beam to beam from a lesser length near the end beams to a greater length midway between the end beams.

In some embodiments, for each of multiple beams, at least the first end and the second end may include, for example, an adhesive. Further, various embodiments may further include, for example, a layer that extends across at least a portion of multiple of the beams, and for multiple of the beams, the layer may extend at least from the first end to the second end, the layer may extend across each beam of the apparatus, or both. Still further, in some embodiments, the beams and connections may be all formed from a common piece of material. Even further, in particular embodiments, multiple of the beams may each have multiple bends.

In some embodiments, the connections between intermediate beams may each have a length perpendicular to the length of the beams and parallel to the width of the beams, and, for multiple of the connections, the length of the connection may be less than one fifth of the length of the beams that the connection is in between. Moreover, in some embodiments, the connections between intermediate beams each have a length perpendicular to the length of the beams and parallel to the width of the beams, and for multiple of the connections, the length of the connection may be greater than the width of the beams that the connection is in between. In addition, or instead, in some embodiments, the connections each have a width perpendicular to the width of the beams and parallel to the length of the beams, and, for multiple connections, the length of the connection is greater than the width of the connection. In particular embodiments, for multiple connections, the length of the connection is less than twice the width of the connection. Even further, in certain embodiments, for each of the multiple intermediate beams, the at least one first connection and the at least one second connection are spaced apart along the length of the beam by the distance of at least four times the width of the beam.

In another specific embodiment, the invention provides a flexible structural apparatus that may include, for example, multiple substantially parallel beams that may include, for instance, two end beams and multiple intermediate beams, wherein the intermediate beams are in between the two end beams, and for multiple beams, the length is at least four times greater than the width and the length is at least five times greater than the height. Such embodiments may also include multiple connections between beams, wherein each connection connects one of the beams to one other of the beams, and wherein each beam has at least one connection to at least one other beam and each intermediate beam has multiple connections to at least two other beams.

In some such embodiments, the width dimension of the connection is no greater than three times the width of either of the beams that the connection is between, and each intermediate beam may be restrained relative to other beams only at the connections. Further, in a number of embodiments, the multiple connections may include, for example, multiple first connections and multiple second connections and multiple intermediate beams may each have at least one first connection to a first adjacent beam and at least one second connection to a second adjacent beam. In many embodiments, for each of the multiple intermediate beams, the at least one first connection and the at least one second connection may be spaced apart along the length of the beam by a distance of at least four times the width of the beam with no other connections therebetween, and from one end beam to the other end beam, the connections may alternate between the at least one first connection and the at least one second connection.

Some embodiments may further include, for example, at least two attachment features that are located at each of the two end beams. In some embodiments, at least one attachment feature that may include, for example, a through hole. In particular embodiments, the apparatus may be used as a spring, for instance.

Still another specific embodiment is a wound covering that may include, for example, a plurality of lateral support members extending between generally opposing sides of the wound covering and having a generally arch shaped cross section so as to form a dome shape. Such embodiments may further include a plurality of coupling members extending between adjacent lateral support members, the coupling members being disposed in an alternating pattern such that the coupling members do not extend in a linear fashion across the wound covering device. Such a wound covering may also include a generally continuous protective layer extending across the wound covering, and a peripheral edge having a generally flat surface formed thereon configured for attachment to skin.

Particular embodiments may further include, for example, a ring pad, and the beams, the connections, the lateral support members, the coupling members, or a combination thereof, may be configured to mount on the ring pad. In some embodiments, the ring pad may include, for example, at least one split. Certain embodiments may further include, for example, at least one hinge configured to attach the ring pad to the beams, the connections, the lateral support members, the coupling members, or a combination thereof. Certain embodiments may include, for example, at least one module fastener configured to connect multiple modules of the wound covering together to form a larger flexible structural apparatus or wound covering. Moreover, in some embodiments, the at least one module fastener may be located in at least one of the coupling members.

In addition, various other embodiments of the invention are also described herein.

The drawings are illustrative and not limiting of the scope of the invention. The embodiments shown accomplish various aspects and objects of the invention. The drawings do not necessarily show each element and aspect of the invention in a single FIGURE, and as such, multiple figures are presented to separately illustrate the various details of various embodiments of the invention in greater clarity. Further, not every embodiment necessarily need accomplish all advantages of the various embodiments of the present invention.

DETAILED DESCRIPTION OF EXAMPLES OF EMBODIMENTS

Particular examples of the invention and the accompanying drawings will now be discussed in reference to the numerals provided therein in sufficient detail so as to enable one skilled in the art to practice these embodiments of the present invention. The drawings and descriptions are exemplary of various aspects of the invention and are not intended to narrow the scope of the appended claims. Various embodiments are or include a flexible structural apparatus. Some embodiments may be used as wound covering devices, for example. Some embodiments may be used as springs or for other purposes, however.

Figure 1:
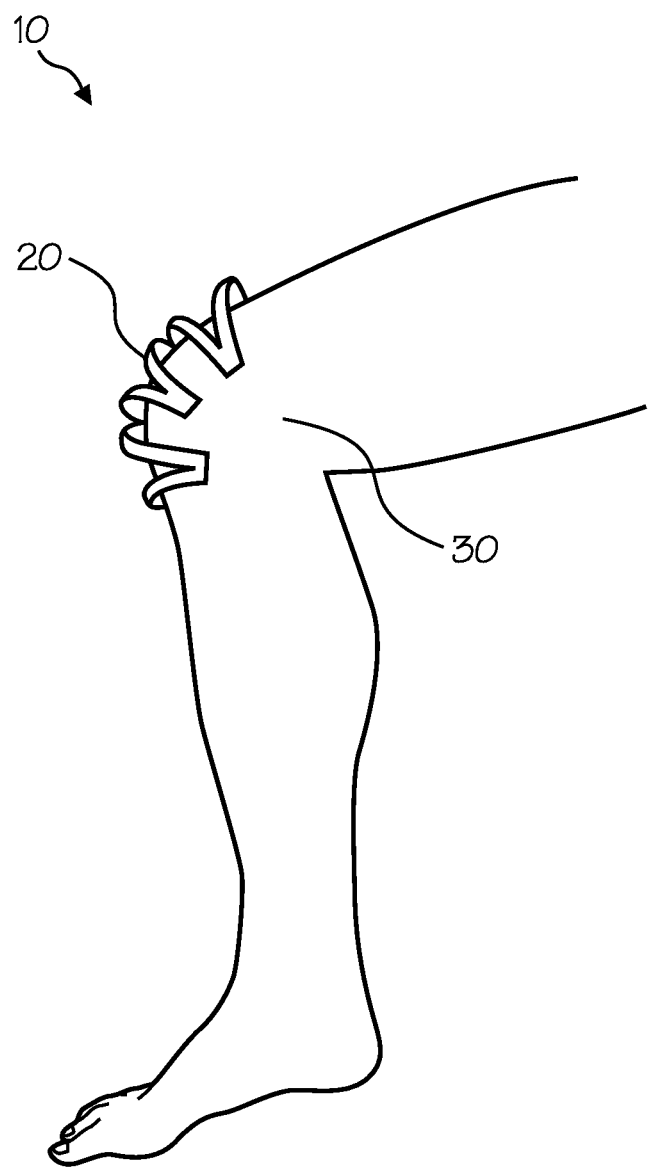
FIG. 1 is a side view of a wound covering placed on a knee, which is an example of a flexible structural apparatus.

Turning now to FIG. 1, a side view of a leg, generally indicated at 10, is shown with a wound covering 20 placed over the knee 30. The wound covering 20 is an example of a flexible structural apparatus, and has a domed shape, which may be shaped such that the wound covering does not touch the knee, in some embodiments, even when the knee is bent. In this embodiment, the wound covering 20 is formed of arch shaped support members which are inter-connected along various locations so that the wound covering 20 can stretch, flex, and generally move with the skin as a person moves. In some embodiments, the wound covering 20 remains separated from the wound when the person moves, preventing damage or disturbance to the wound and helping to keep objects from touching or applying a force to the wound.

Although not shown in many of the drawings, in some embodiments, the wound covering 20 may include a flexible covering which may extend over the outer surface of the wound covering to keep dirt and debris out of the wound, for example. In various embodiments, such a flexible covering may be located over or under the beams and connections (e.g., support members and coupling members) or may weave between adjacent beams or groups of (e.g., of two, three, four, five, six, eight, or ten) beams, for example. In some embodiments, the wound covering 20 may be a separate structure which may be used in combination with covering such as gauze or the like. In various embodiments, the wound covering may be kept from touching the wound in order to promote healing of the wound and/or minimize irritation of the wound, as examples. The covering may be sufficiently flexible, in some embodiments, to not interfere with the movement of the wound covering.

Figure 2:
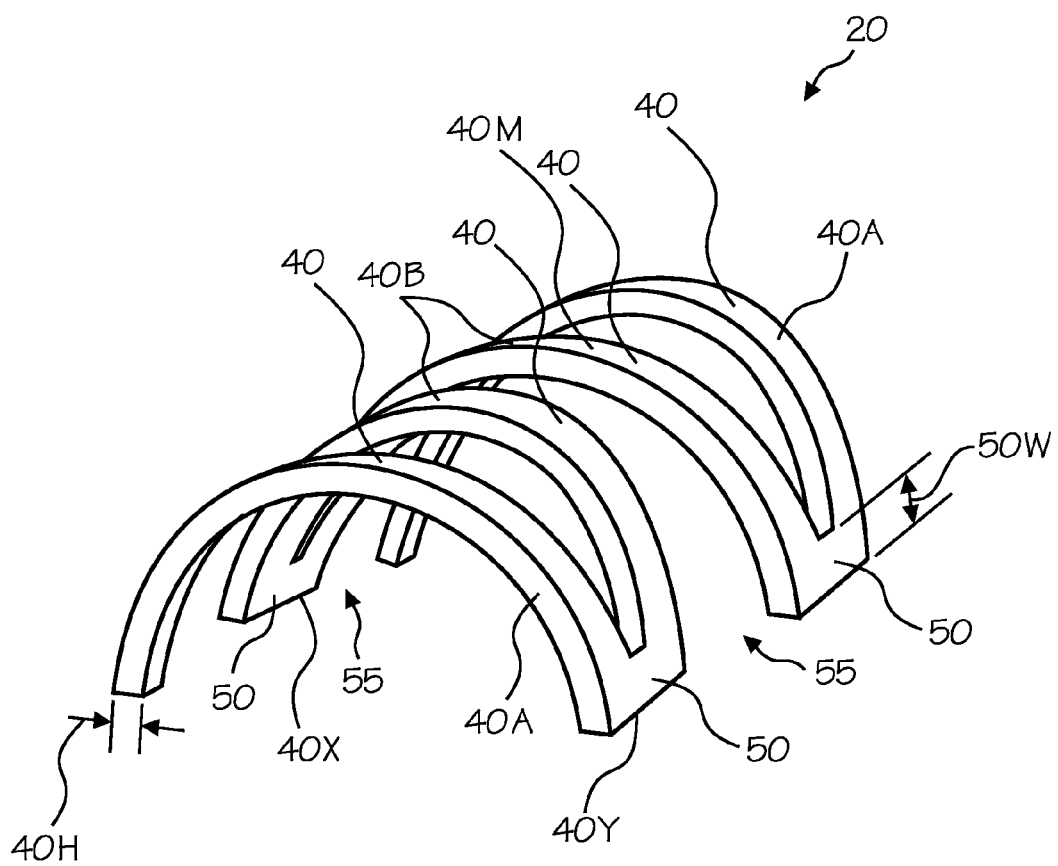
FIG. 2 is an isometric view of the wound covering of FIG. 1.

Turning now to FIG. 2, there is shown an isometric view of the wound covering 20 of FIG. 1. The wound covering 20, in this embodiment, is formed with lateral support members 40 (e.g., beams) which extend between opposing sides of the wound covering. The lateral support members, in the embodiment illustrated, are generally arch shaped (e.g., cambered), as this shape extends upwardly and over a wound so as to not contact the wound while providing good mechanical strength and resistance to collapse, as examples. The lateral support members 40, in this embodiment, are interconnected at various locations by coupling members (e.g., connections) such as the coupling members 50 placed near the ends of the support members 40. The coupling members 40, in this embodiment, generally do not contact each other continuously along a portion of the wound covering 20, but rather, leave spaces 55 between adjacent coupling members 50 so that the wound covering 20 can compress at the space 55 in addition to being able to stretch. The use of alternating coupling members and spaces in connecting the support members 40, in this embodiment, allows the wound covering 20 to twist, flex, bend, and stretch to a high degree while experiencing relatively small bends in each particular support member or coupling member. The coupling members help keep the support members from bending over sideways, in this embodiment, if a compressive force or downward force is applied to the top of the wound covering 20, and help spread the force between adjacent support members, allowing the wound covering 20 to prevent unintentional contact with the wound or application of force directly thereto.

Figure 3:
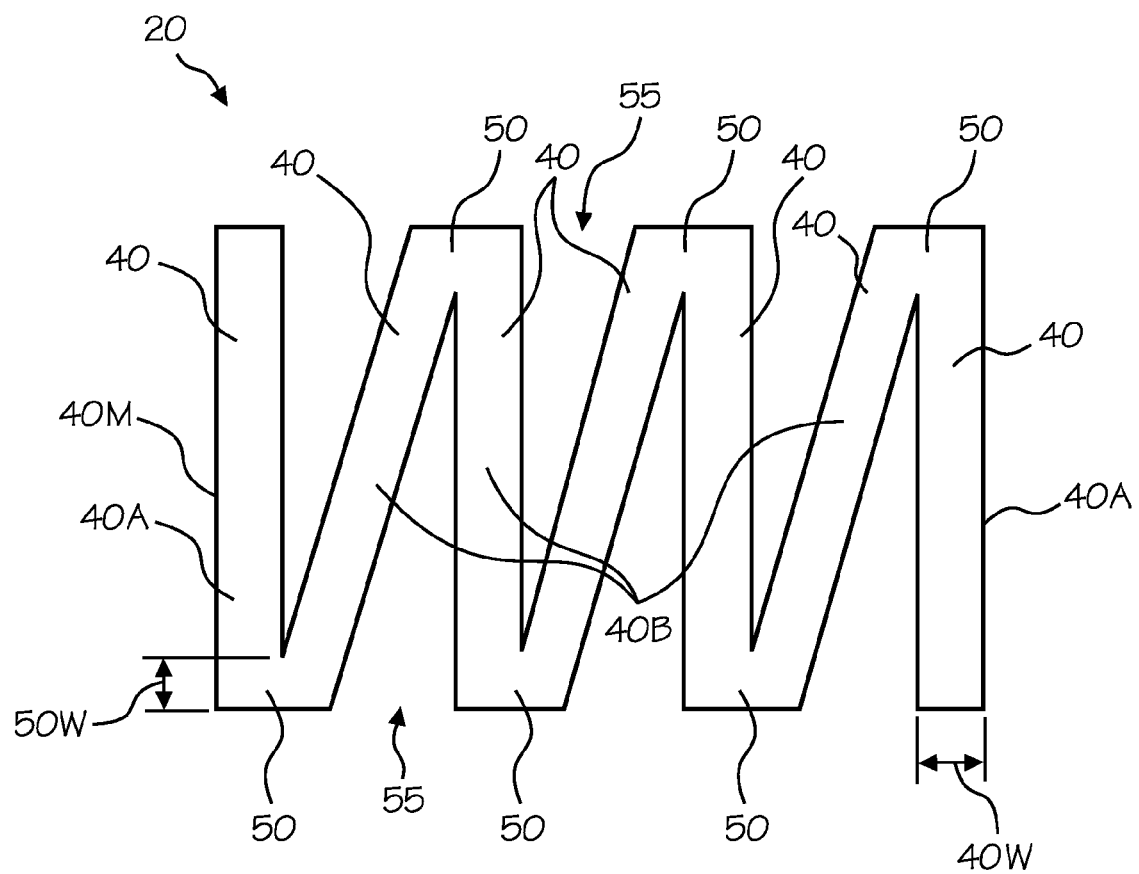
FIG. 3 is a top view of the wound covering of FIG. 1.

FIG. 3 is a top view of the wound covering 20 of FIGS. 1 and 2. It can be observed how the placement of the lateral support members 40 (e.g., beams) and connecting members 50 (e.g., connections) provides a wound covering 20 which can stretch, compress, flex, and twist in nearly any direction. This allows the wound covering 20 to follow the movement of the skin, in some embodiments, even if the skin is on a joint or another body location where the skin moves a lot with body movement. The flexibility of the wound covering 20 may be altered by adjusting the thickness or width of the lateral support members 40 and the coupling members 50. Thus, in a number of embodiments, a wound covering 20 may be achieved which is very flexible in allowing skin movement and which is strong to resist collapse, for example.

Figure 4:
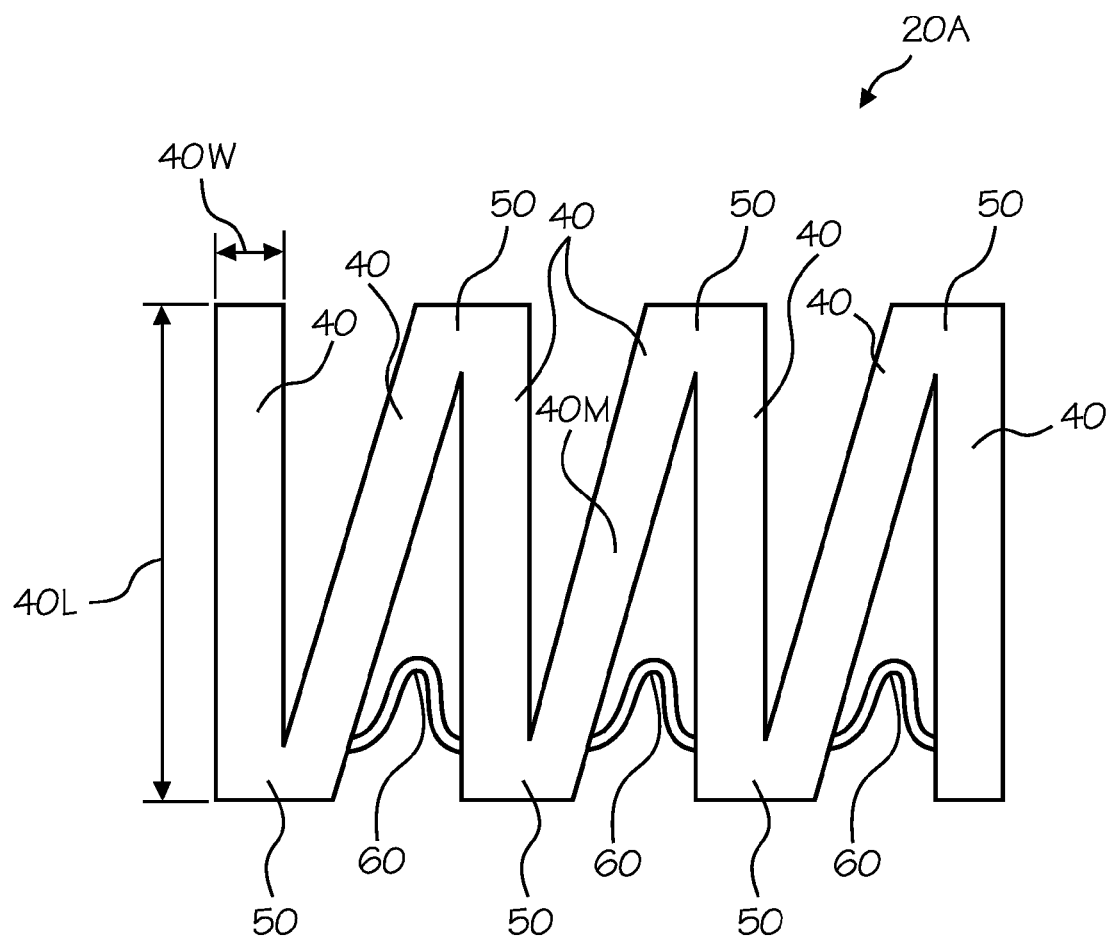
FIG. 4 is a top view of another wound covering similar to that of FIG. 1, which is another example of a flexible structural apparatus.

FIG. 4 is a top view of an alternative embodiment of the wound covering 20 which is similar to that of FIG. 3. The wound covering 20A includes lateral support members 40 (e.g., beams) and coupling members 50 (e.g., connections), which may be similar to those of FIG. 3, and also includes curved coupling members 60. The curved coupling members 60 provide flexibility similar to that of a spring, and thus provides some additional bracing between lateral support members, in this embodiment, while allowing for easy flexing and stretching of the wound covering 20A. The curved coupling members 60 may be used to allow for easy stretching or flexing of the wound covering 20A within a limited range of motion while effectively limiting motion outside of that range of motion, for example.

Figure 5:
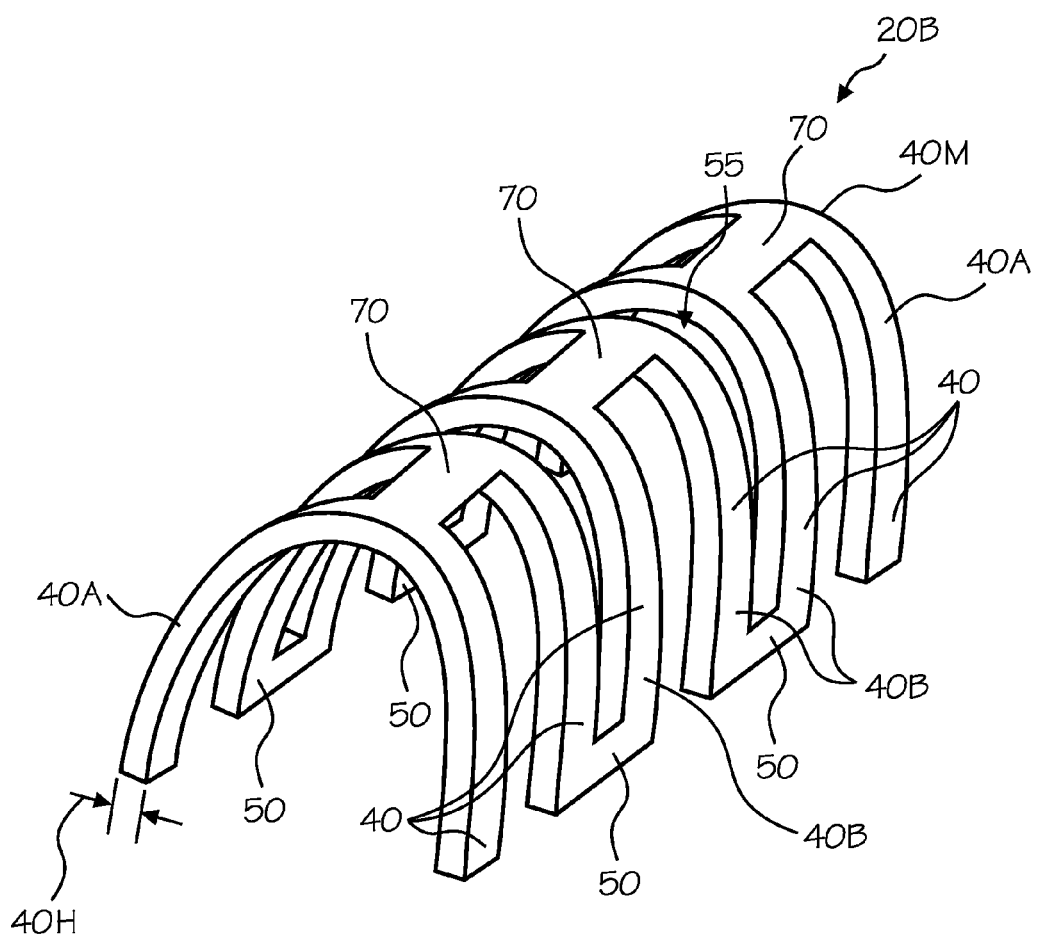
FIG. 5 is a an isometric view of another wound covering, which is another example of a flexible structural apparatus.

FIG. 5 is an isometric view of another wound covering 20B. The wound covering 20B includes lateral support members 40 (e.g., beams), end coupling members 50 (e.g., first connections) as well as central coupling members 70 (e.g., second connections). As can be seen, in this particular embodiment, the lateral support members 40 form a tunnel shaped structure which may protect the wound from accidental contact, for example. As can be seen, in this embodiment, the end coupling members 50 and the central coupling members 70 are formed alternately with spaces 55 between the lateral support members 40. This structure allows the wound covering 20B to stretch and flex with the movement of the skin.

Figure 6:
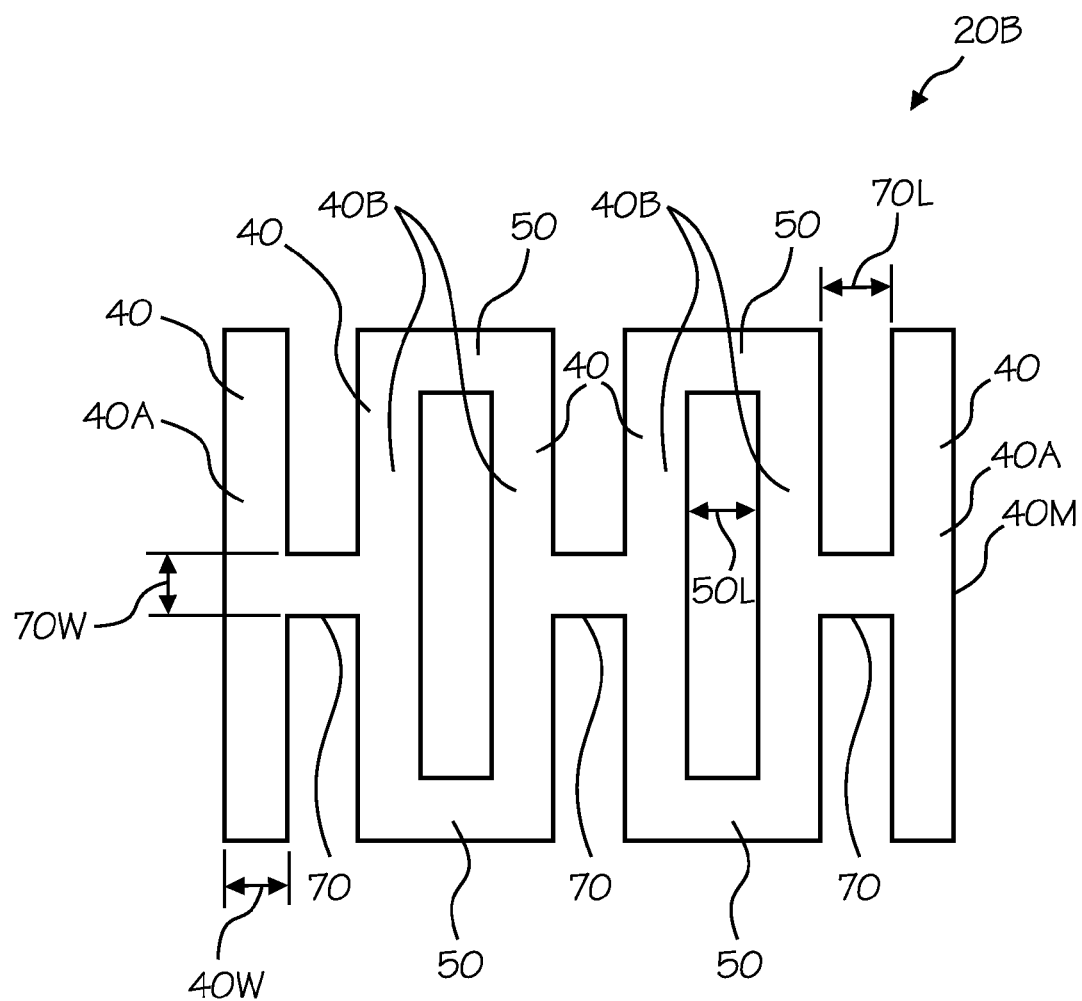
FIG. 6 is a top view of the wound covering of FIG. 5.

Turning now to FIG. 6, a top view of the wound covering 20B of FIG. 5 is shown. It is apparent in this view how the end coupling members (e.g., first connections) and the central coupling members (e.g., second connections) connect the lateral support members (e.g., beams) in this embodiment. Stretching or bending movements of the wound covering 20B may involve some bending of the coupling members, the lateral support members, or both. Because of the way that the coupling members (e.g., connections) 50 and 70 are alternately disposed between the lateral support members 40, the wound covering 20B can undergo a high degree of bending or stretching by a number of the various members bending a small amount. This allows the wound covering 20B to bend and flex sufficiently to accommodate body movement of a person wearing the device, for example.

Although the central coupling member 70 (e.g., second connection) is shown in the center in the drawings, in other embodiments, the central coupling members 70 may be offset from the center, multiple central coupling members may be used per wound covering 20B, or both. In various embodiments, the number and spacing of the various coupling members or connections (or the central coupling members in particular) may be determined by the desired size of the wound covering 20B, by the desired amount or range of flexibility, by the desired stiffness, or a combination thereof, as examples. Further, in some embodiments, one or more of the central coupling members 70 (e.g., second connections) may be angled or curved similar to the curved coupling member 60 of FIG. 4, as another example.

Figure 7:
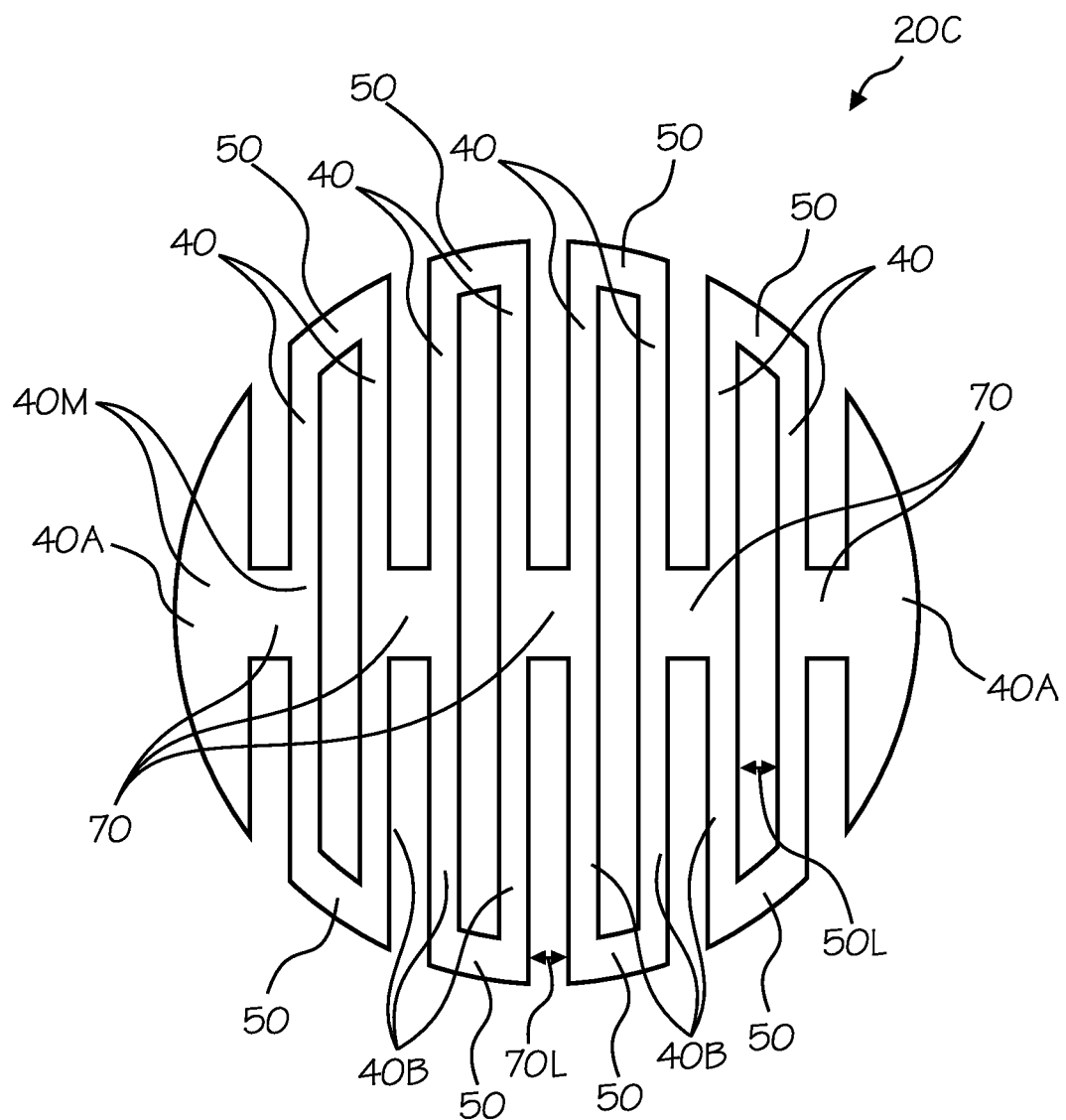
FIG. 7 is a top view of a circular wound covering, which is another example of a flexible structural apparatus.

FIG. 7 is a top view of another wound covering 20C, which may be similar in some respects to that of FIG. 5. The wound covering 20C, in this embodiment, is generally circular or in the shape of an oval as viewed from above, and may present a dome shaped covering as viewed from the end or side of the device. The lateral support members 40 (e.g., beams, which may be cambered), are formed with different lengths, in this embodiment, to achieve the circular shape shown and may have different heights. The wound covering 20C may provide a similar degree of flexibility and protection as described before, for example, and provides a shape which may be better suited to some types of wounds, for instance. In some embodiments, the various straight (generally tunnel shaped) wound coverings discussed herein (e.g., such as that of FIG. 5) may (e.g., alternatively) be formed with semi-circular ends (e.g., as shown in FIG. 7) so that the ends of the wound covering are closed and provide a more gentle transition when extending from the skin. In some embodiments, the lateral support members 40A (e.g., end beams) on the ends of the wound covering 20C may be modified such as to provide a larger base and thereby accommodate a more secure attachment to the skin.

Figure 8:
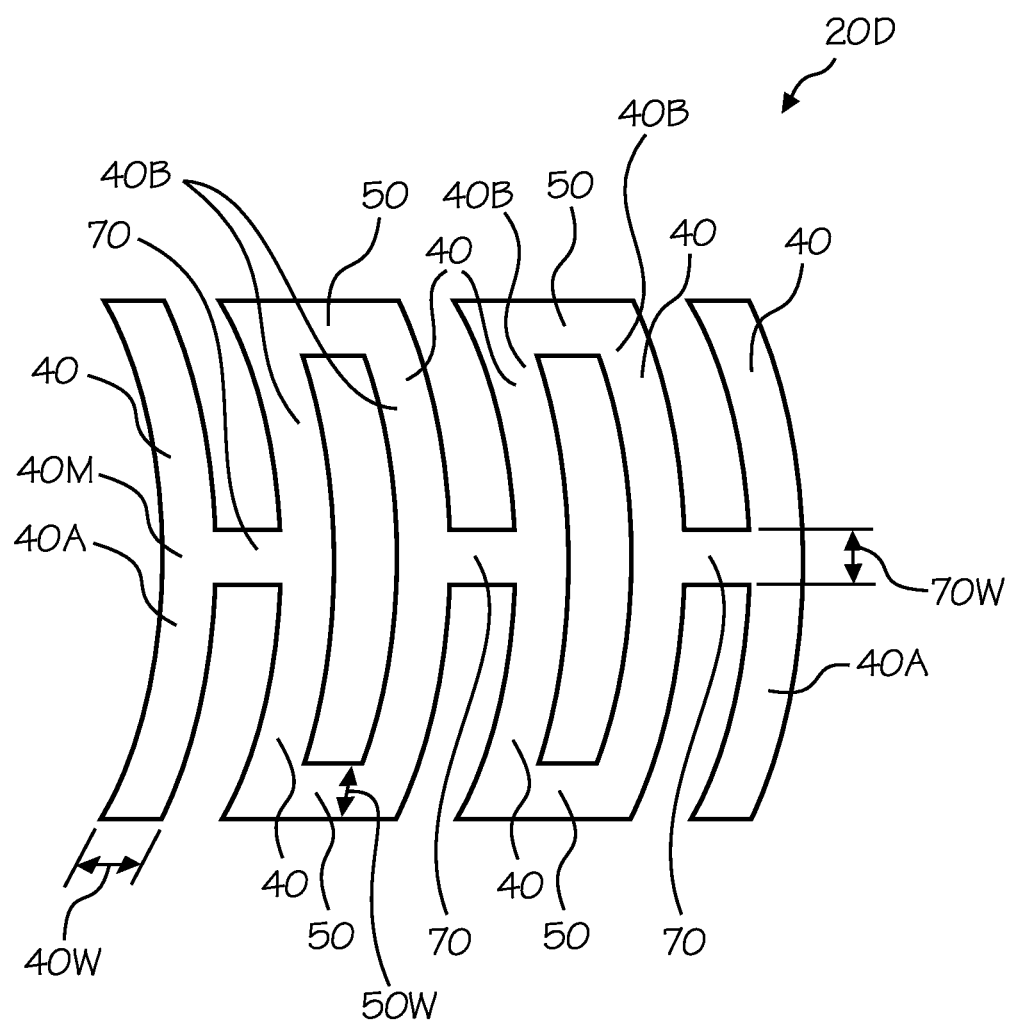
FIG. 8 is a top view of another wound covering, which is another example of a flexible structural apparatus.

Turning now to FIG. 8, a top view of another wound covering 20D similar to that of FIG. 5 is shown. In this embodiment, the lateral support members 40 (e.g., beams) are curved as viewed from above. Curved lateral support members 40 may provide some increased flexibility and may also reduce the likelihood that a planar object such as a ruler passes therethrough and contacts the wound.

Figure 9:
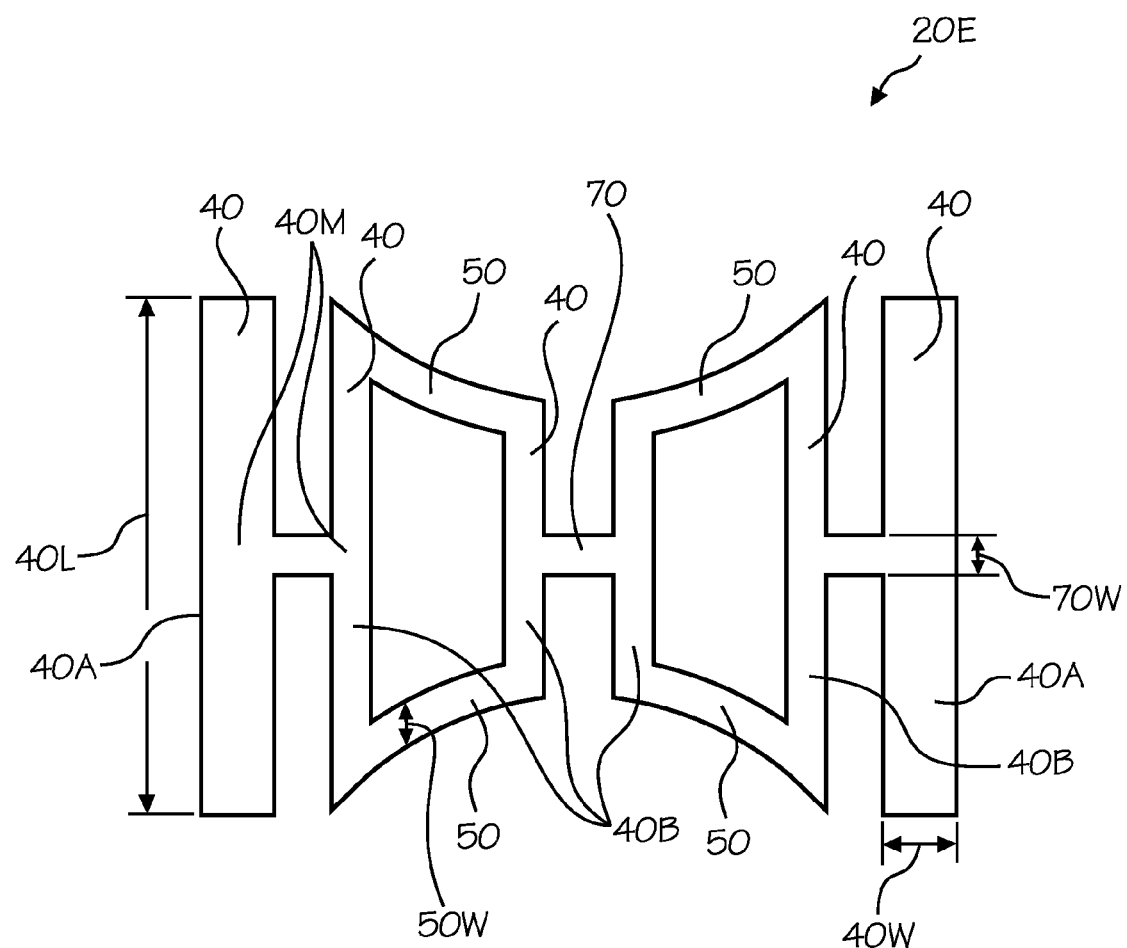
FIG. 9 is a top view of another wound covering, which is another example of a flexible structural apparatus.

FIG. 9 is a top view of another wound covering 20E, which may be similar to that of FIG. 5 in some respects. The wound covering 20E, in this embodiment, has a concave shape (e.g., at the ends of beams or support members 40), and may fit better than other embodiments between two fingers or another narrow location to protect a wound, for example.

Figure 10:
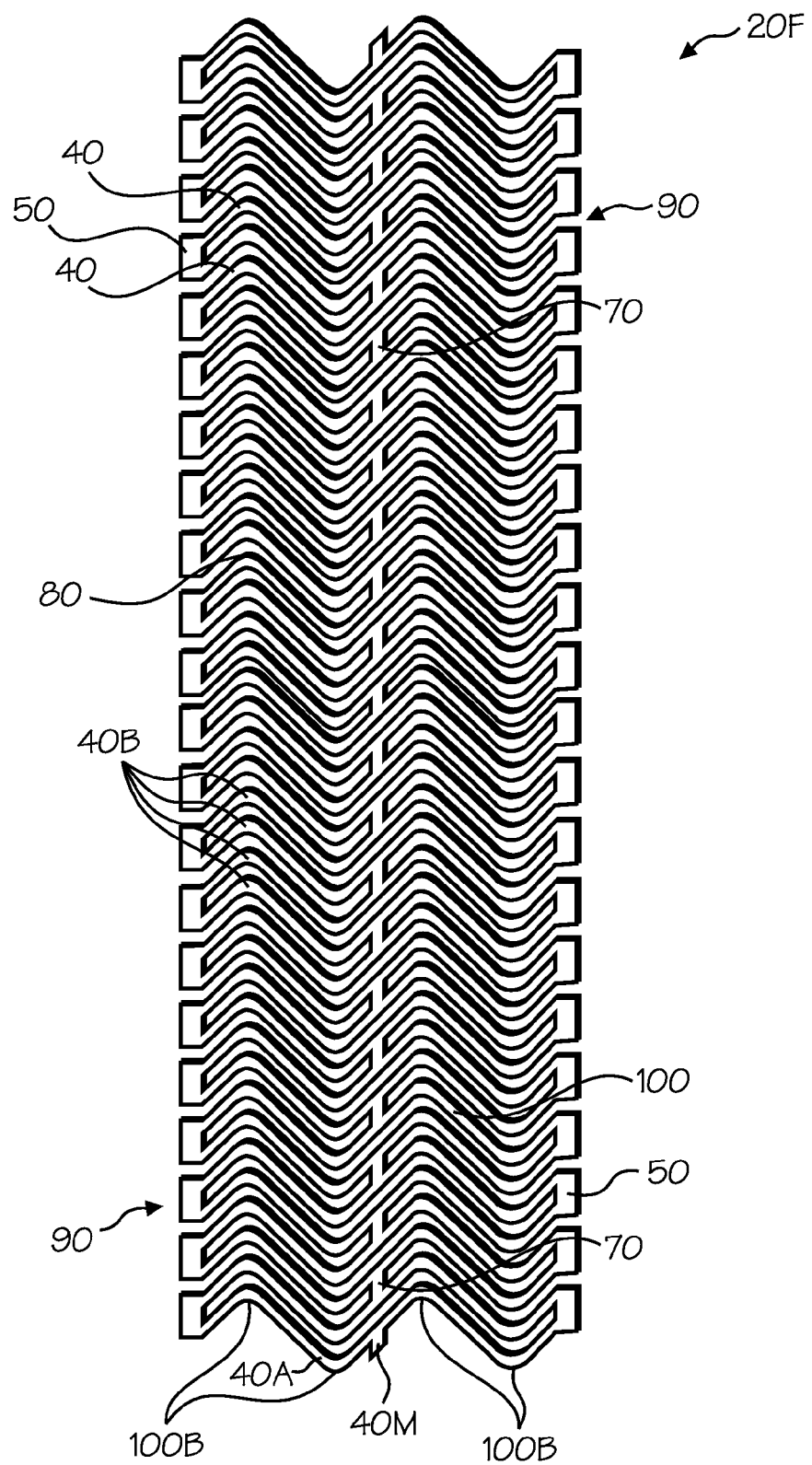
FIG. 10 is a top view of a section of another wound covering, which is another example of a flexible structural apparatus.
Figure 11:
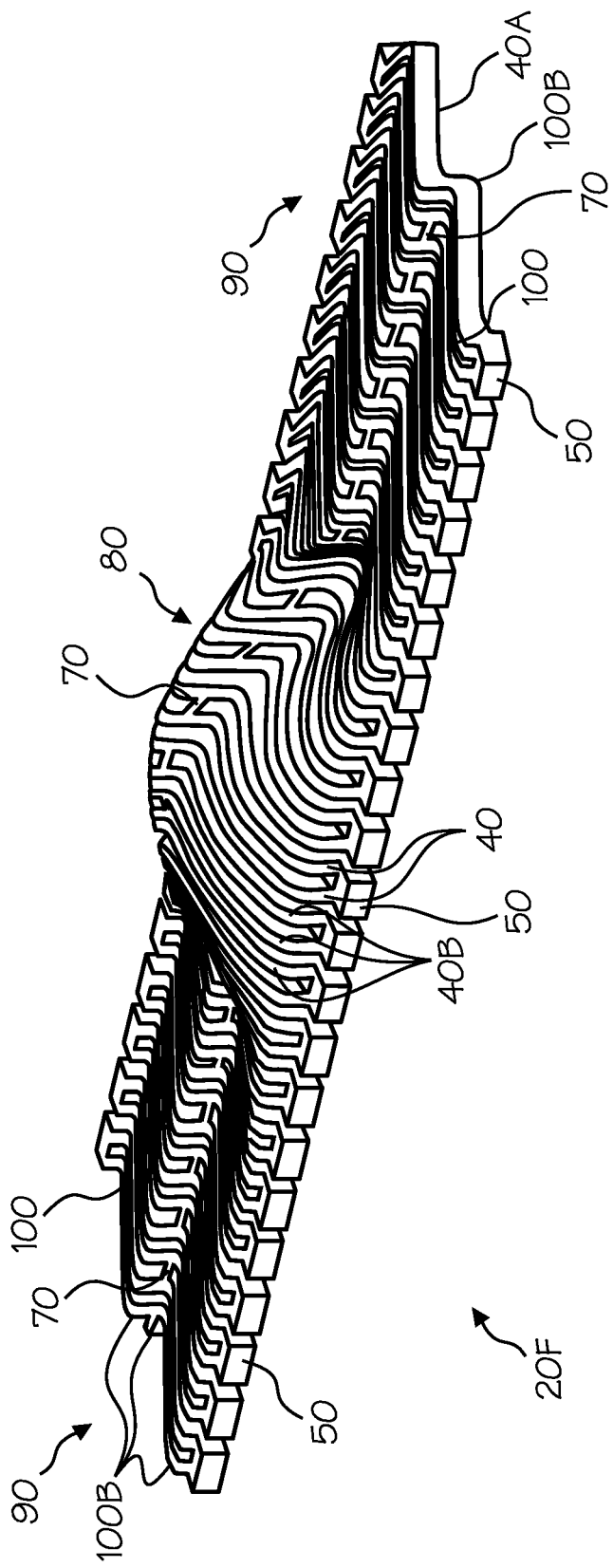
FIG. 11 is an isometric view of the wound covering of FIG. 10.

FIGS. 10 and 11 show another flexible structural apparatus or wound covering 20F. Apparatus 20F includes lateral support members 40 (e.g., beams), end coupling members 50 (e.g., first connections), and central coupling members 70 (e.g., second connections) as have been discussed. FIG. 11 shows how the apparatus, in this embodiment, forms a dome 80 which may extend above a wound, for example, to protect the wound. The wound covering 20F may extend beyond the dome 80 as indicated at 90 in order to provide additional surface area for securely attaching the wound covering apparatus to the skin, for example. This may prevent the wound covering 20F from accidentally being torn or otherwise removed form the skin, for instance. The extended areas 90 are formed, in this embodiment, with lateral extending members 100 (e.g., beams), end coupling members 50, and central coupling members 70 so that the extended areas 90 can flex and stretch in a manner similar to that of the raised dome 80.

Figure 12:
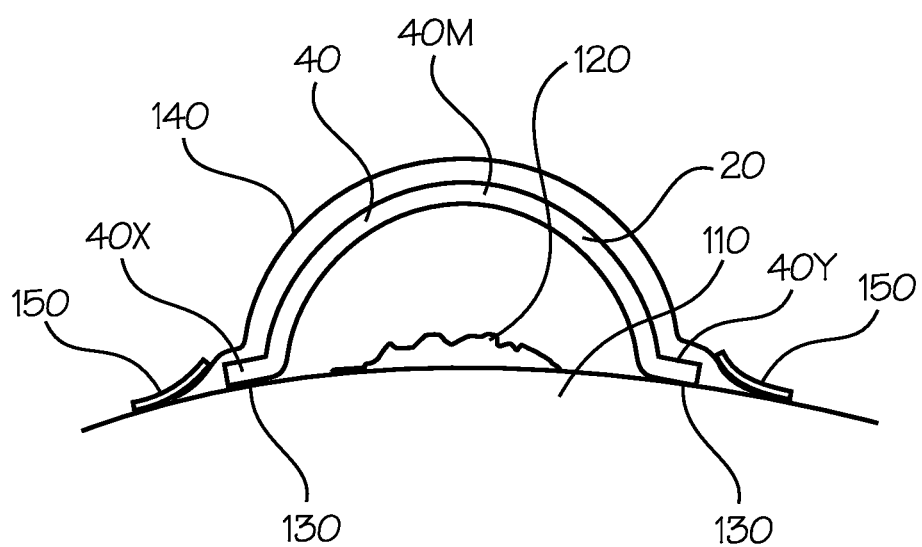
FIG. 12 is an end view of a wound covering over a wound.
Figure 13:
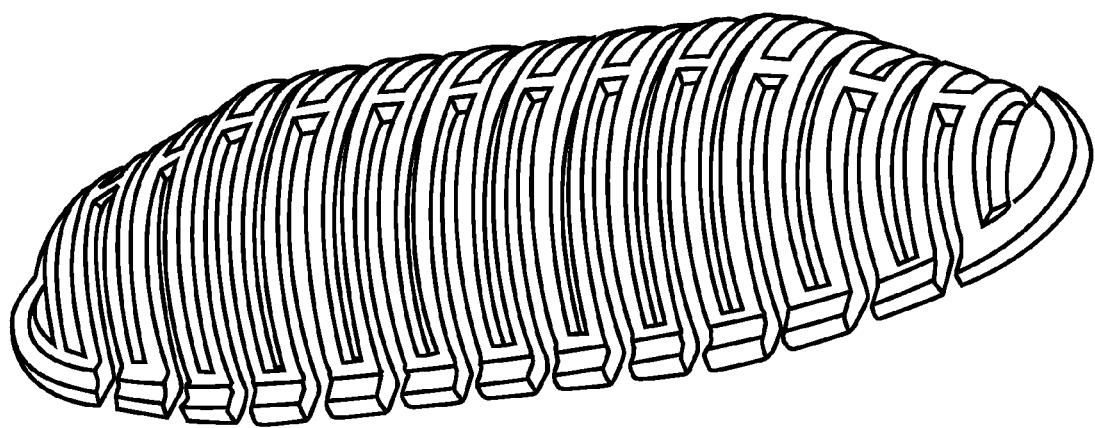
FIG. 13 is an isometric view of a flexible structural apparatus which may be used as a wound covering, for example.
Figure 14:
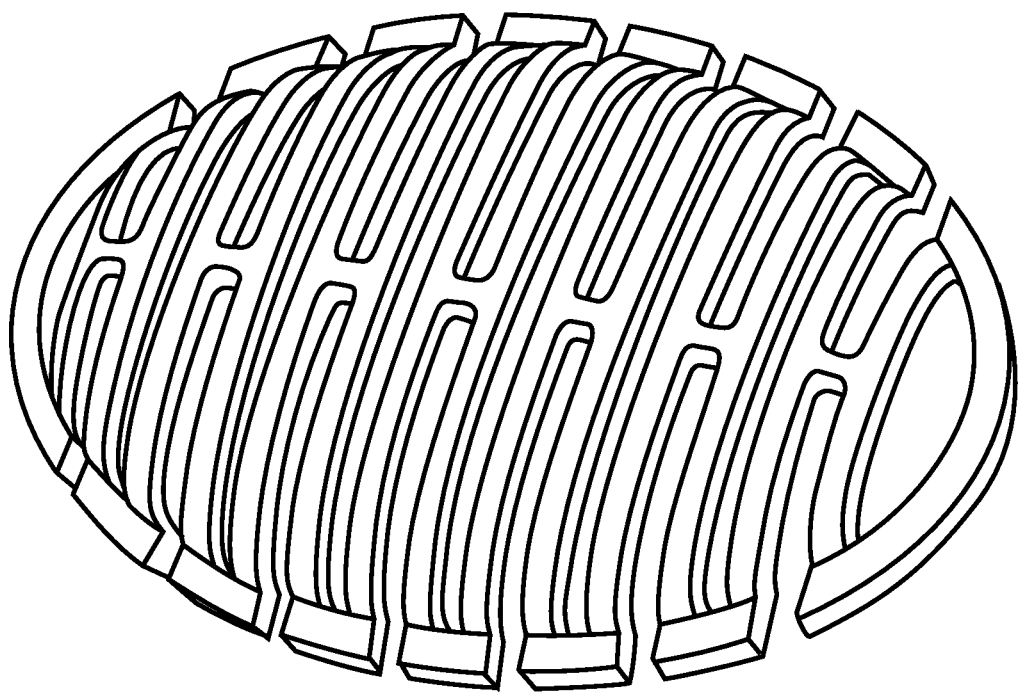
FIG. 14 is an isometric view of a flexible structural apparatus which may be used as a wound covering, for example.
Figure 15:
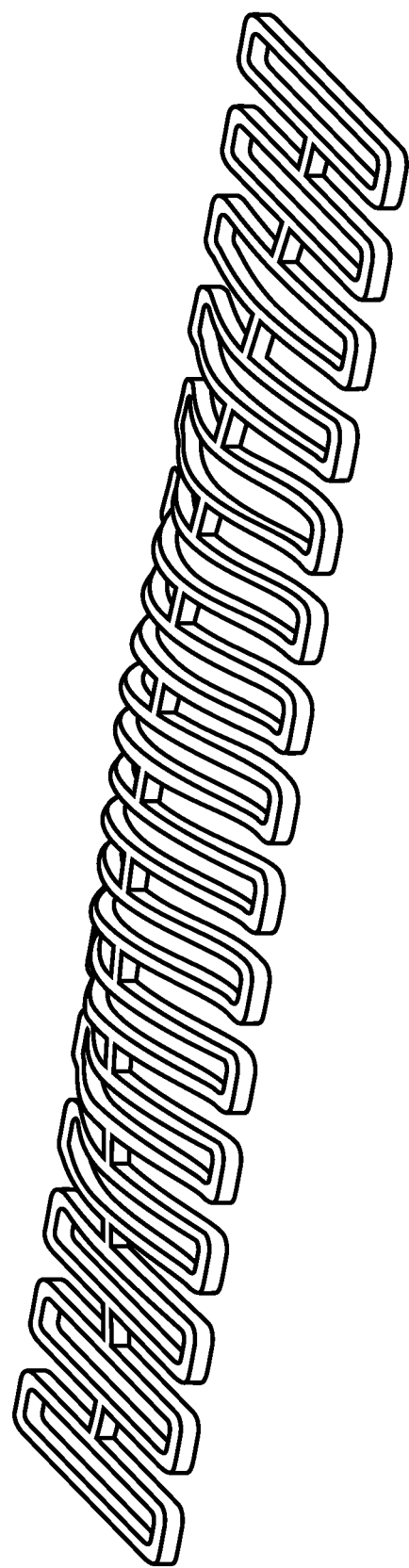
FIG. 15 is an isometric view of a flexible structural apparatus which may be used as a wound covering, for example.
Figure 16:
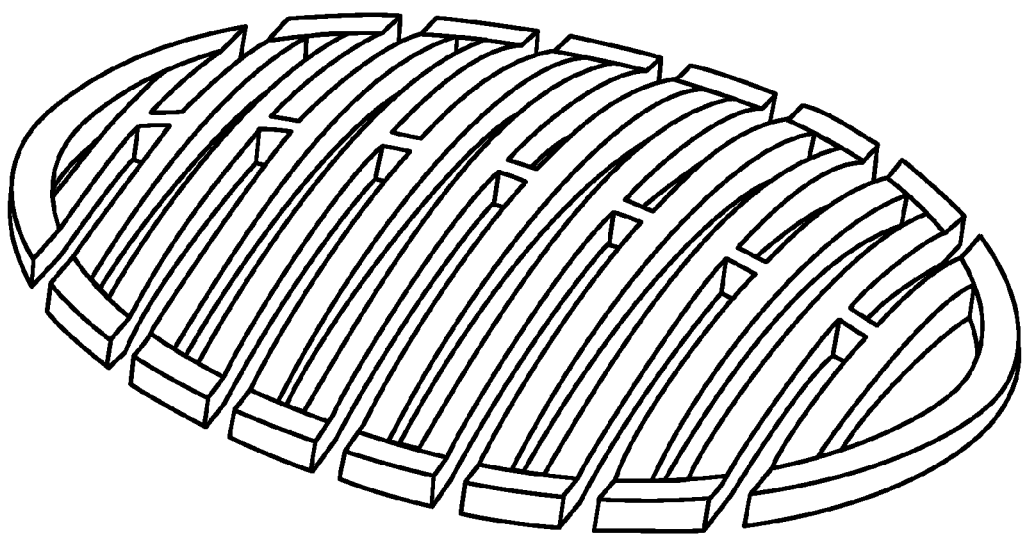
FIG. 16 is an isometric view of a flexible structural apparatus which may be used as a wound covering, for example.
Figure 17:
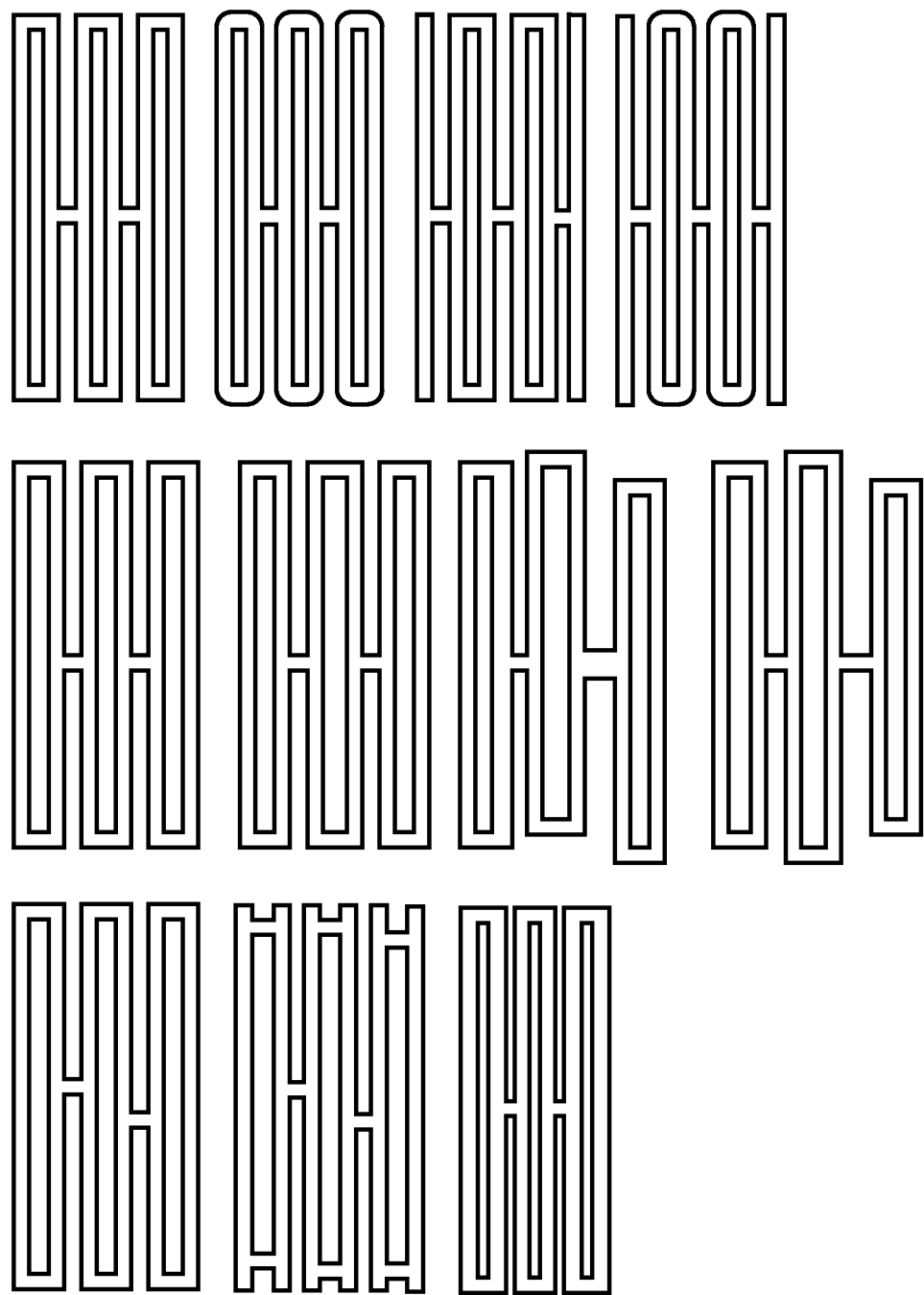
FIG. 17 includes top views of several embodiments of flexible structural apparatuses which may be used as a wound covering, for example.

Turning now to FIG. 12, a partially cut away view of a wound covering 20 as disclosed in the previous figures is shown. The wound covering 20 is attached to skin 110 so as to protect a wound 120. The wound covering 20 may be attached to the skin 110 with an adhesive 130, for example. The wound covering 20 may include a generally continuous protective layer 140, in some embodiments. The protective layer 140 may be (or include) gauze or other appropriate medical covering, and may serve to keep contaminants such as dirt or liquids from coming in contact with the wound 120, for example. Depending on the application, the protective layer 140 may be an integral part of the wound covering 20 or may be a separate structure which may be applied to the wound covering 20 and skin 110 with medical tape 150 or the like after applying the wound covering 20 to the skin, as examples. In some embodiments or applications (e.g., veterinary applications) a tape or wrap may be used that sticks to itself better than to other materials, or is more cohesive than adhesive, for example. Coban is an example of such a tape or wrap, for instance. Such a tape or wrap may be used to avoid or reduce pulling on fur, hair, or skin when removed, to facilitate reuse after inspection of the wound, or a combination thereof, as examples.

In some embodiments, a structural apparatus or wound covering device may be covered with spines or spikes. For example, in wound covering devices for use on animals, spines or spikes may keep the animal from licking or otherwise touching the device. Other embodiments may use a bad tasting substance applied to the device, as another example, or may have an increased surface roughness, as yet another example.

In a number of embodiments, the wound covering 20 forms a protective barrier above the wound 120 which isolates the wound from contact as well as from contaminants. Ointment or the like may be placed on the wound 120 and remain on the wound. In some embodiments, wound covering 20 may be advantageous because it may provide a strong structure which is resistant to collapse and deformation while still being very flexible and allowing various types of movement of the skin 110, such as stretching, skewing, bending, twisting, etc.

Besides use as a wound covering, various embodiments of the invention have other uses. Some embodiments may be used as springs or as devices for protecting certain body parts (e.g., from physical trauma in high-risk activities such as sports), as examples. Other uses may be apparent to a person of skill in the art.

Various embodiments are or include a flexible structural apparatus. Examples are shown in FIGS. 1-17 and 20-27. In a number of embodiments, for example, such an apparatus may include multiple substantially parallel beams (e.g., support members 40) which may include two end beams (e.g., 40A) and multiple intermediate beams (e.g., 40B), for instance. In some embodiments, the intermediate beams (e.g., 40B) are in between the two end beams (e.g., 40A), for example. In various embodiments, each beam (e.g., 40) may have a length (e.g., 40L), a width (e.g., 40W), and a height (e.g., 40H). In some embodiments, for example, for multiple of the beams, the length (e.g., 40L) may be at least four times greater than the width (e.g., 40W), the length (e.g., 40L) may be at least four times greater than the height (e.g., 40H), or both. In some embodiments, the length (e.g., 40L) may be at least three, five, six, seven, eight, nine, ten, 12, 15, 20, or 25 times greater than the width (e.g., 40W), the length may be at least three, five, six, seven, eight, nine, ten, 12, 15, 20, or 25 times greater than the height (e.g., 40H), or a combination thereof, as other examples.

Many embodiments also include multiple connections (e.g., connecting members or coupling members 50, 70, etc.) between beams (e.g., 40). In a number of embodiments (e.g., shown in FIGS. 1-4), for example, each connection (e.g., 50) connects one of the beams to one other of the beams. Further, in some embodiments, each beam (e.g., 40) has at least one connection (e.g., 50 or 70) to at least one other beam, for example, and each intermediate beam (e.g., 40B) has multiple connections to at least two other beams. Examples are shown in FIGS. 5-11, 13-17, and 20-27. Still further, in some embodiments, each connection (e.g., 50 or 70) has a width dimension (e.g., 50W or 70W) that may be parallel to the length (e.g., 40L) of the beams (e.g., 40), for example. In some embodiments, the width dimension (e.g., 50W or 70W) of the connection (e.g., 50 or 70) may be no greater than one fourth of the length of either of the beams (e.g., 40) that the connection may be between, for instance. In other (or the same) embodiments, the width dimension (e.g., 50W or 70W) of the connection (e.g., 50 or 70) may be no greater than one third, one fifth, one sixth, one eighth, one tenth, $\frac{1}{12}$, $\frac{1}{16}$, $\frac{1}{20}$, or $\frac{1}{25}$ of the length of either of the beams (e.g., 40) that the connection may be between, as other examples. In some embodiments, each intermediate beam (e.g., 40B) may be restrained relative to other beams (e.g., 40A or 40B) only at the connections (e.g., 50 or 70), for example. This, among other things, distinguishes, for example, roof structures, where a sheet of roofing material typically restrains beams or trusses along their length, for instance.

In some embodiments, the multiple connections (e.g., 50 and 70) include different classifications of connections, or connections at different locations (e.g., relative to each other) or connecting to different beams (e.g., 40), such as (e.g., multiple) first connections (e.g., 50) and second connections (e.g., 70), for example. In certain embodiments, for instance, multiple intermediate beams (e.g., 40B) each have at least one first connection (e.g., 50) to a first adjacent beam (e.g., 40A or 40B)) and at least one second connection (e.g., 70) to a second adjacent beam (e.g., on the other side). As used herein, two beams (e.g., 40) are said to be adjacent if there is no other substantially parallel beam in between them and the two beams are separated by a distance no greater than one half of the length of the shorter of the two beams. Further, as used herein, substantially parallel means either that the two beams, for example, are parallel to within 10 degrees, or that the beams can be flexed into a parallel position without the average stress in any cross section of the beams or connections exceeding the yield stress. In particular embodiments, as used herein, substantially parallel means either that the two beams, for example, are parallel to within 10 degrees, or that the beams can be flexed into a parallel position without exceeding 10 percent of the yield stress anywhere in the beams or connections.

In particular embodiments, for example, for each of the multiple intermediate beams (e.g., 40B), the at least one first connection (e.g., 50) and the at least one second connection (e.g., 70) are spaced apart along the length (e.g., 40L) of the beam by a distance of at least one fourth of the length of the beam with no other connections therebetween. On the other hand, in some embodiments, for each of the multiple intermediate beams (e.g., 40B), the at least one first connection (e.g., 50) and the at least one second connection (e.g., 70) are spaced apart along the length (e.g., 40L) of the beam by a distance of at least three quarters, two thirds, one half, one third, one fifth, one sixth, one eighth, or one tenth, of the length of the beam, as other examples, (e.g., with no other connections therebetween). In some embodiments, from one end beam (e.g., 40A) to the other end beam, for example, the connections alternate between the (e.g., at least one) first connection (e.g., 50) and the (e.g., at least one) second connection (e.g., 70). Examples are shown, for instance, in FIGS. 5-11, 13-17, and 20-27. (In FIGS. 1-4, connections 50 on one side of the apparatus or the beams 40 may be considered the first connections, and connections 50 on the other side may be considered the second connections.)

In a number of embodiments, multiple intermediate beams (e.g., 40B) each have at least two first connections (e.g., 50) to a first adjacent beam (e.g., on one side) and at least one second connection (e.g., 70) to a second adjacent beam (e.g., on the other side), for example. Examples are shown, for instance, in FIGS. 5-11, 13-17, and 20-27. In certain embodiments, for instance, for each of the multiple intermediate beams (e.g., 40B), each of the at least two first connections (e.g., 50) and the at least one second connection (e.g., 70) are spaced apart along the length (e.g., 40L) of the beam by a distance between connections (e.g., 50 and 70) of at least one fourth of the length (e.g., 40L) of the beam (e.g., 40B). In other (or the same) embodiments, for each of the multiple intermediate beams (e.g., 40B), each of the at least two first connections and the at least one second connection are spaced apart along the length of the beam by a distance between connections of at least two fifths, one third, one fifth, one sixth, one eighth, or one tenth of the length of the beam, as other examples. In some embodiments, from one end beam (e.g., 40A) to the other end beam, the connections alternate between the at least two first connections (e.g., 50) and the at least one second connection (e.g., 70), for example. Again, examples are shown, for instance, in FIGS. 5-11, 13-17, and 20-27.

In some embodiments, each beam (e.g., 40) has a first end (e.g., 40X) and a second end (e.g., 40Y), and for each of the multiple intermediate beams (e.g., 40B), for instance, one of the first connections (e.g., 50) may be located along the length of the beam within a distance of no more than one fifth of the length (e.g., 40L) of the beam from the first end (e.g., 40X). In other (or the same) embodiments, one of the first connections (e.g., 50) may be located along the length (e.g., 40L) of the beam (e.g., 40) within a distance of no more than one third, one fourth, one sixth, one seventh, one eighth, one tenth, $\frac{1}{15}$, or $\frac{1}{20}$ of the length (e.g., 40L) of the beam from the first end (e.g., 40X), as other examples. Further, in some embodiments, for each of the multiple intermediate beams, one of the first connections (e.g., 50) may be located along the length (e.g., 40L) of the beam (e.g., 40) within a distance of no more than one fifth of the length of the beam from the second end (e.g., 40Y). In other (or the same) embodiments, one of the first connections (e.g., 50) may be located along the length of the beam within a distance of no more than one third, one fourth, one sixth, one seventh, one eighth, one tenth, $\frac{1}{15}$, or $\frac{1}{20}$ of the length of the beam from the second end (e.g., 40Y), as other examples. Further, in some embodiments, for each of the multiple intermediate beams, one of the first connections (e.g., 50) may be located at the first end (e.g., 40X) of the beam, one of the first connections (e.g., 50) may be located at the second end (e.g., 40Y) of the beam, or both. Examples are shown, for instance, in FIGS. 5-11, 13-17, and 20-27.

In particular embodiments, each beam (e.g., 40) has a midpoint (e.g., 40M), and (e.g., for each of the multiple intermediate beams 40B) at least one second connection (e.g., 70) may be located along the length (e.g., 40L) of the beam within a distance of no more than one fifth of the length of the beam from the midpoint (e.g., 40M). In other (or the same) embodiments, at least one second connection (e.g., 70) may be located along the length (e.g., 40L) of the beam (e.g., 40) within a distance of no more than one third, one fourth, one sixth, one seventh, one eighth, one tenth, 1/15, or 1/20 of the length of the beam from the midpoint (e.g., 40M), as other examples. In some specific embodiments, one second connection (e.g., 70) may be located along the length (e.g., 40L) of the beam at the midpoint (e.g., 40M), for example. Examples are shown, for instance, in FIGS. 5-11, 13-17, and 20-27.

In a number of embodiments, each (i.e., every) intermediate beam (e.g., 40B) has at least two first connections (e.g., 50) to a first adjacent beam (e.g., 40) and at least one second connection (e.g., 70) to a second adjacent beam (e.g., 40). Further, in some embodiments, multiple of the intermediate beams (e.g., 40B) each have precisely two first connections (e.g., 50) to the first adjacent beam, and precisely one second connection (e.g., 70) to the second adjacent beam, or both. Examples are shown, for instance, in FIGS. 5-11, 13-17, and 20-27. In other (or the same) embodiments, multiple or each of the intermediate beams (e.g., 40B) each have precisely one, three, four, five, six, seven, eight, nine or ten first connections (e.g., 50) to the first adjacent beam, and precisely two, three, four, five, six, seven, eight, nine or ten second connections (e.g., 70) to the second adjacent beam, or a combination thereof, as other examples. Some embodiments have one more of the first connections (e.g., 50) than the second connections (e.g., 70), for instance.

In some specific embodiments multiple intermediate beams (e.g., 40B) each have precisely one first connection (e.g., 50 on side 40X) to a first adjacent beam (e.g., 40) and precisely one second connection (e.g., 50 on side 40Y) to a second adjacent beam (e.g., 40). Examples are shown in FIGS. 1-3, for instance. In some such embodiments, for each of the multiple intermediate beams (e.g., 40B), the one first connection and the one second connection are spaced apart along the length (e.g., 40L) of the beam by a distance of at least one third of the length of the beam. On the other hand, in some embodiments, for each of the multiple intermediate beams, the one first connection and the one second connection are spaced apart along the length of the beam by a distance of at least one quarter of the length of the beam, at least one half of the length of the beam, at least five eights of the length of the beam, at least three fourths of the length of the beam, at least seven eights of the length of the beam, or at least nine tenths of the length of the beam, as other examples. Examples are shown, for instance, in FIGS. 1-3.

In various embodiments, for each of the multiple intermediate beams (e.g., 40B), the first connection may be located along the length (e.g., 40L) of the beam within a distance of no more than one fifth of the length of the beam from the first end (e.g., 40X). In other (or the same) embodiments, for each of the multiple intermediate beams, for example, the first connection may be located along the length of the beam within a distance of no more than one third, one fourth, one sixth, one seventh, one eighth, one tenth, 1/12, 1/15, 1/20, or 1/25 of the length of the beam from the first end (e.g., 40X), as other examples. Further, in some embodiments, for each of the multiple intermediate beams (e.g., 40B), the second connection may be located along the length of the beam within a distance of no more than one fifth of the length (e.g., 40L) of the beam from the second end (e.g., 40Y). And in some embodiments, for each of the multiple intermediate beams, for example, the second connection may be located along the length of the beam within a distance of no more than one third, one fourth, one sixth, one seventh, one eighth, one tenth, 1/12, 1/15, 1/20, or 1/25 of the length of the beam from the second end (e.g., 40Y), as other examples. In particular embodiments, for each of the multiple intermediate beams, the first connection may be located at the first end (e.g., 40X) of the beam, the second connection may be located at the second end (e.g., 40Y) of the beam, or both, as further examples. Again, examples are shown, for instance, in FIGS. 1-3.

In many embodiments, the connections (e.g., 50, 70, or both) are straight (e.g., perpendicular to the length 40L of the beams), but in other embodiments, the connections may be curved (e.g., in two or three dimensions). An example are the curved coupling members 60 shown in FIG. 4. Connections 50 in FIG. 9 are also curved. Various curved connections (e.g., 50 or 70) may have a shape of an arch, part of a sine wave, an arc, part of a parabola, part of a hyperbola, part of a helix, part of a spiral, etc.

In some embodiments, some, multiple, or all of the intermediate beams (e.g., 40B) may each have a preformed camber in a direction of the height (e.g., 40H) of the beam (i.e., in the plane of the height 40H and length 40L of the beam and visible when viewed from the side). Different embodiments may have different amounts of camber. Examples are shown in FIGS. 1, 2, 5, 11, 12, 13-16, 20, 23-25, and 27, for instance. Beams (e.g., 40) may be higher in the middle (e.g., at 40M) than at the ends (e.g., 40X and 40Y), for example, and may have a constant radius of curvature (e.g., form an arc) or may have a parabolic shape (e.g., concave downwards), as examples. In some embodiments, different intermediate beams (e.g., 40B) may have a different amount of camber (e.g., in the direction of the height of the beam). In some specific embodiments, for example, the amount of camber varies from beam to beam from a lesser amount of camber (e.g., in vertical dimension) near the end beams to a greater amount of camber midway between the end beams. Examples are shown in FIGS. 11, 13-16, 23, 24, and 25, for instance. Further, in some embodiments, different intermediate beams (e.g., 40B) have a different length. In some embodiments, for example, the lengths (e.g., 40L) of the beams varies from beam to beam from a lesser length near the end beams to a greater length midway between the end beams. Examples are shown in FIGS. 7, 13, 14, 16, 24, and 25, for instance.

Figure 24:
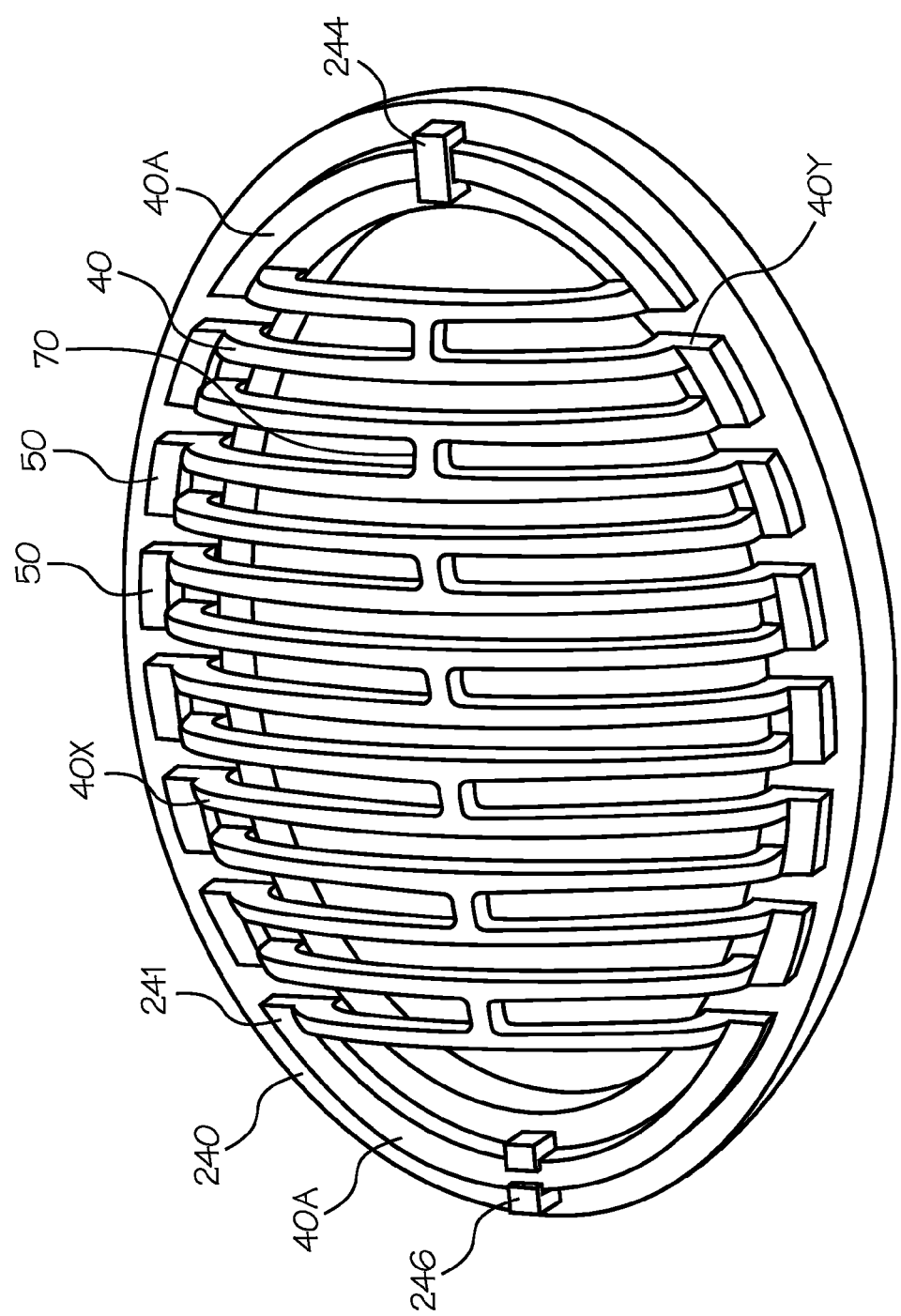
FIG. 24 is an isometric view of a flexible structural apparatus which has a ring pad, a ring pad snap fastener, and a hinge.
Figure 25:
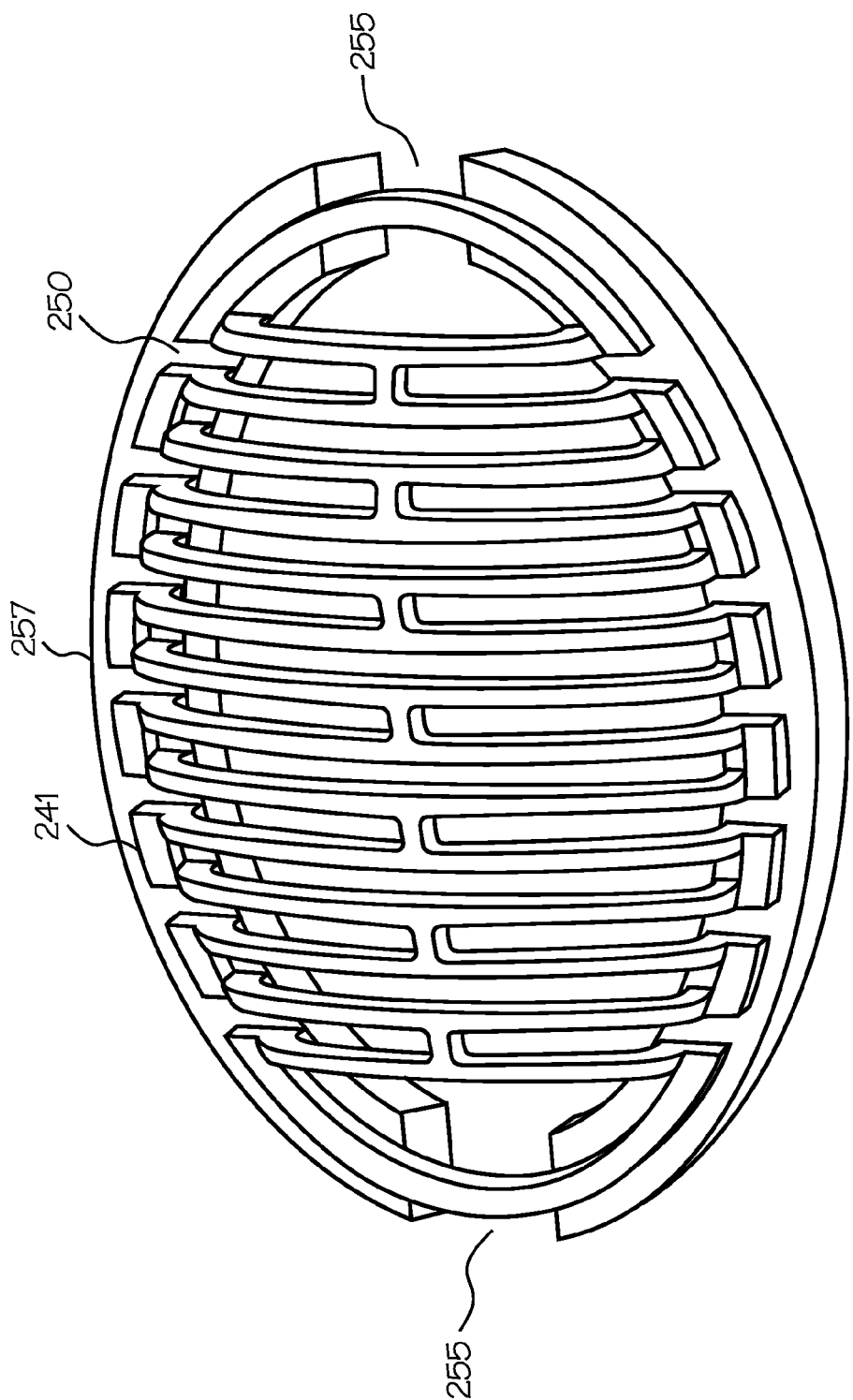
FIG. 25 is a an isometric view of a flexible structural apparatus which has a ring pad having two splits forming two segments.

Some embodiments include an adhesive (e.g., 130 shown in FIG. 12). For instance, wound covering devices may have an adhesive at the perimeter (e.g., at ends 40X and 40Y, at end beams 40A, or both) to attach the device to the patient's skin or other tissue (e.g., as shown in FIG. 12), or to a ring pad (e.g., 240 and 250 as shown in FIGS. 24 and 25). In some embodiments, each beam (e.g., 40) has a first end (e.g., 40X) and a second end (e.g., 40Y), and, for each of multiple beams (e.g., 40B), for instance, (or for all beams 40, in some embodiments) at least the first end (e.g., 40X) and the second end (e.g., 40Y) include the adhesive (e.g., 130), for example. In some embodiments, the beams (e.g., 40) and connections (e.g., 50, 70, or both) are all formed from a common piece of material. In particular embodiments, this material may be plastic, metal, or a composite material, as examples.

In some embodiments, various layers of different materials may be used for the beams (e.g., 40), connections (e.g., 50, 70, or both), or both. In some embodiments, for instance, a sandwich material or structure may be used. For example, some embodiments may have a higher strength top and bottom layer with a lighter spacer material in between. In some embodiments, for example, a body material may be coated with a coating that may add strength, reduce or increase friction, or the like. Some embodiments may have fiber reinforcement, which may be parallel to the beams (e.g., in the direction of the length, 40L), parallel to the connections (e.g., in the direction 40W), concentrated at the top, concentrated at the bottom, or a combination thereof, as examples.

Some embodiments may be shaped flat on the bottom, while other embodiments may have a different shape on the bottom, for example, for matching a patient's body in the case of a wound covering device. In some embodiments, the bottom may be concave downward or upward when viewed from the side or from the end, as examples. Some embodiments may have a bottom shape that is concave upward when viewed from the side and concave downward when viewed from the end, or vice versa, as other examples. Particular embodiments may be moldable, for example, heat moldable or UV moldable. In heat-moldable embodiments, the apparatus (e.g., beams 40, connections 50 or 70, or both) may be made of a material that can be heated (e.g., in hot or boiling water) and bent by the user, and that will retain the shape that it is bent to when the material returns to room temperature or body temperature, for example. For wound coverings, for instance, shaping the apparatus to fit the body part (e.g., knee 30 shown in FIG. 1) may reduce stress on adhesive (e.g., 130) attaching the apparatus to the body part, for instance. In UV-moldable embodiments, the apparatus (e.g., beams, connections, or both) may be made of a material that can be exposed to ultra violet light and bent by the user, and that will retain the shape that it is bent to when the apparatus is placed into service. Certain embodiments may be made of a radiation-curable material that may moldable to the desired shape by the user and then may be cured to retain its shape or to become less ductile by exposure to radiation such as ultraviolet light. The user that molds such embodiments may be the doctor, nurse, or patient, for example, in wound covering applications, and the apparatus may be shaped to better fit the body part that the wound covering device is used on.

Some embodiments may include an outer layer (e.g., layer 140 shown in FIG. 12) extending over multiple of the beams (e.g., 40). In some embodiments, for example, for each of multiple beams, for instance, the outer layer (e.g., 140) extends at least from the first end (e.g., 40X) to the second end (e.g., 40Y). More generally, a number of embodiments include a layer (e.g., 140) that extends across at least a portion of multiple of the beams (e.g., 40). In various embodiments, for example, the layer extends under, in between, or over the beams (or a combination thereof). In certain embodiments, the layer may weave between the beams, or between groups of beams, for instance. These groups of beams may include, for example, two, three, four, five, six, seven, eight, nine, ten, 12, or 15 beams, as examples. In particular embodiments, the layer (e.g., 140) may attach to some or all of the beams (e.g., 40), connections (e.g., 50, 70, or both), or both, for example, while in other embodiments, the layer may not attach to the beams, may not attach to the connections, or both, for instance. Further, in some embodiments, the outer layer (e.g., 140) extends across, past, or over each beam of the apparatus. In certain embodiments, the outer layer may be fabric or cloth or may be a thin flexible sheet, as examples.

In some embodiments, multiple beam and connection structures, as described herein, may be used with one over the top of the other. Beams in the different layers may be substantially parallel, substantially perpendicular (e.g., when viewed from above), or at an angle in between, as examples, to obtain the desired stiffness in various directions. Angles between beams in the different layers may be, for example, 0, 10, 20, 30, 40, 45, 50, 60, 70, 80, or 90 degrees, as examples, or within a range therebetween. In different embodiments, one, two, three, four, five, or more separate layers of beams and connections may be used, for instance. In some embodiments, different layers may be connected to each other, while in other embodiments, different layers may not connect. Further, in some embodiments, an upper layer may completely cover a lower layer, while in other embodiments, an upper layer may cover only part of a lower layer. In some embodiments, different materials may be used for the different layers.

Figure 18:
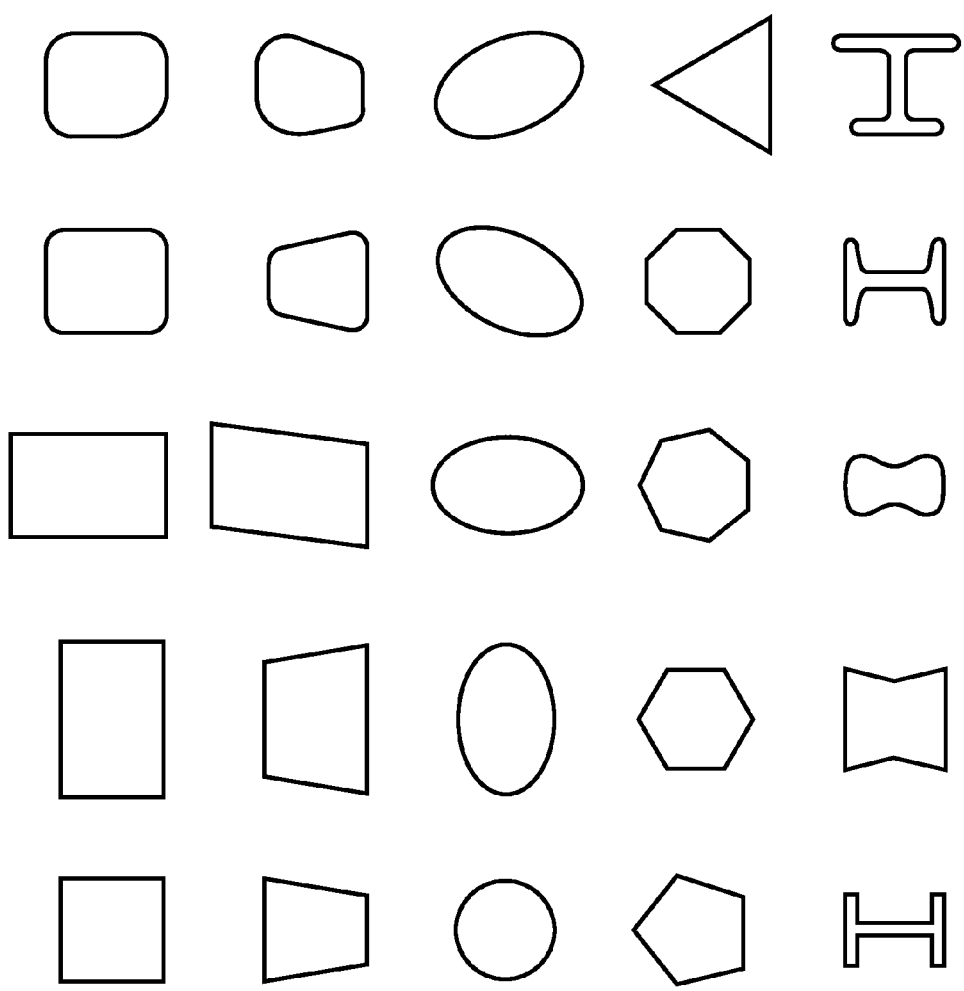
FIG. 18 includes multiple cross-sectional views of various different solid cross sections that may be used for beams, connections, ring pad, or a combination thereof, in different embodiments.
Figure 19:
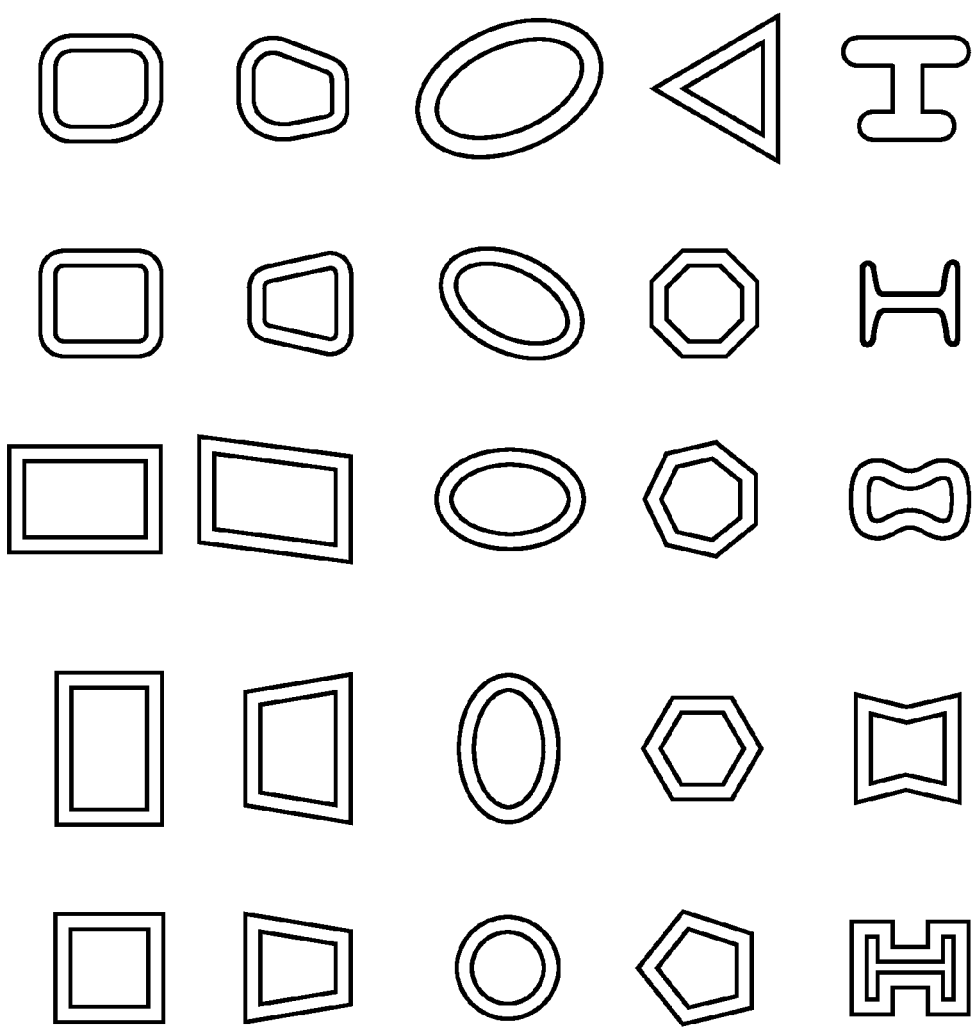
FIG. 19 includes multiple cross-sectional views of various different hollow cross sections that may be used for beams, connections, ring pad, or a combination thereof, in different embodiments.
Figure 20:
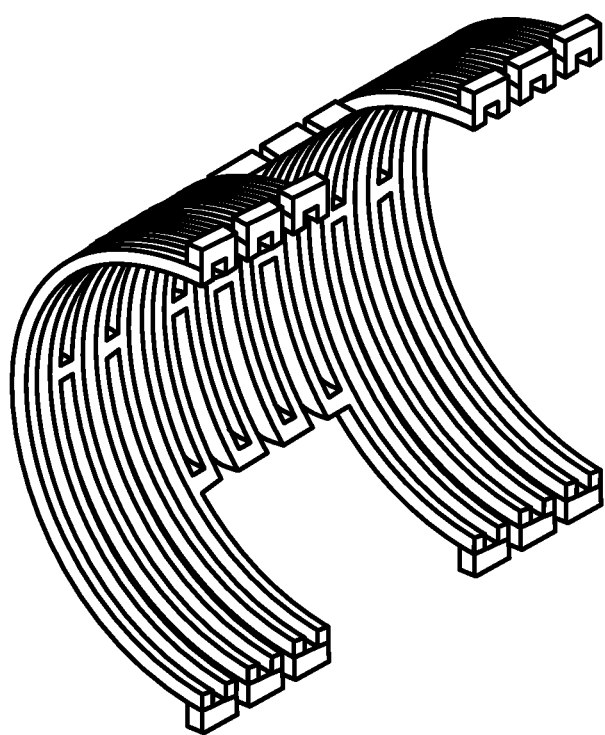
FIG. 20 is a an isometric view of a flexible structural apparatus which may be used as a wound covering, for example.

In some embodiments, multiple (e.g., some or all) of the beams (e.g., 40) each have a substantially constant cross section along the length of the beam. In other embodiments, the cross section may change along one or more beams, for example, from a smaller cross section at the ends to a greater cross section in the middle of the beams. In still other embodiments, the cross section may change along one or more beams, for example, from a larger cross section at the ends to a smaller cross section in the middle of the beams. Examples of cross sections of beams (e.g., 40), connections (e.g., 50, 70, or both), ring pads (e.g., 240 or 250), or a combination thereof, are shown in FIGS. 18 and 19, for instance. In different embodiments, such cross sections may be solid or hollow, as examples. In some applications, it may be advantageous to use a cross section for beams, connections, or both, that has a greater height (e.g., 40H) than width (e.g., for beams, 40W, for connections, 50W or 70W). Such a cross section may provide a greater stiffness in resistance to forces perpendicular to the wound or the skin, for example (e.g., in the direction parallel to 40H), while providing greater flexibility or less stiffness in a direction parallel to the wound or skin and perpendicular to the beams, for example (e.g., in the direction of 40W). In applications where less flexibility is desired, (e.g., in a direction parallel to the wound or skin and perpendicular to the beams) the width (e.g., 40W) of beams, connections, or both may be increased, and the number of beams, connections, or both, may be reduced. In some embodiments, this may result in a width (e.g., 40W) of the beams (e.g., 40), connections (e.g., 50W or 70W), or both, that is greater than the height.

In particular embodiments, multiple (e.g., some or all) of the beams each have multiple bends (e.g., in a horizontal direction, or visible when viewed from above). Examples are bends 100B shown, for instance, in FIGS. 10 and 11, which illustrate a zigzag shape when viewed from the top. In some embodiments, for example, each of the beams has precisely four (4) bends (e.g., which may or may not include bends at the ends of the beams, which may be of a lesser angle, for instance, 45 degrees). Other embodiments may have one, two, three, five, six, seven, eight, nine, ten, 12, 15, or 20 bends per beam, as other examples. In some embodiments, multiple of the bends (e.g., 100B) may be greater than 45 degree bends, greater than 60 degree bends, less than 135 degree bends, less than 120 degree bends, or a combination thereof, as examples. In some specific embodiments, multiple of the bends (e.g., 100B) are approximately 90 degree bends (e.g., as shown). As used herein "approximately 90 degrees" means between 80 degrees and 100 degrees. In some embodiments, at least for multiple of the beams (e.g., 40), the beams are nested together so that the bends (e.g., 100B) in adjacent beams substantially line up. Examples are shown, for instance, in FIGS. 10 and 11.

In some embodiments, the connections (e.g., 50, 70, or both, at least between intermediate beams 40B) each have a length (e.g., 50L or 70L) perpendicular to the length (e.g., 40L) of the beams (e.g., 40) and parallel to the width (e.g., 40W) of the beams. In some embodiments, for example, for multiple of the connections (e.g., 50, 70, or both), the length (e.g., 50L or 70L) of the connection may be less than one fifth of the length (e.g., 40L) of the beams (e.g., 40) that the connection is in between. In other (or the same) embodiments, the length of the connection may be less than one third, one fourth, one sixth, one seventh, one eighth, one tenth, $\frac{1}{12}$, $\frac{1}{15}$, or $\frac{1}{20}$ of the length of the beams that the connection is in between. In some embodiments, at least for multiple of the connections, the length (e.g., 50L or 70L) of the connection may be greater than the width (e.g., 40W) of the beams that the connection may be in between, or may be about equal to the width of the beams that the connection is in between. As used herein "about equal to" means plus or minus 50 percent of the smaller dimension.

In a number of embodiments, the connections (e.g., 50, 70, or both) between intermediate beams (e.g., 40B) each have a width (e.g., 50W, or 70W) perpendicular to the width (e.g., 40W) of the beams (e.g., 40) and parallel to the length (e.g., 40L) of the beams. In some embodiments, for multiple connections, for instance, the width (e.g., 50W or 70W) of the connection may be about equal to the width (e.g., 40W) of the beams that the connection is in between, for example. In some embodiments, (e.g., for multiple connections) the length (e.g., 50L or 70L) of the connection may be greater than the width (e.g., 50W or 70W) of the connection, for example. On the other hand, in some embodiments, for multiple connections, the length of the connection (e.g., 50L or 70L) may be less than twice the width (e.g., 50W or 70W) of the connection. In other (or the same) embodiments, however, the length of the connection may be less than 1.25, 1.5, 1.75, 2.25, 2.5, 3, 4, or 5 times the width of the connection, as other examples.

In some embodiments, (e.g., for each of the multiple intermediate beams 40B) the at least one first connection (e.g., 50) and the at least one second connection (e.g., 70) are spaced apart along the length of the beam by the distance of at least four times the width (e.g., 40W) of the beam. In other (or the same) embodiments, the at least one first connection and the at least one second connection are spaced apart along the length of the beam by the distance of at least three, five, six, seven, eight, nine, ten, 12, 15, 20, or 25 times the width of the beam, as other examples. In certain embodiments, (e.g., for multiple of the beams 40) the length (e.g., 40L) may be at least four times greater than the width (e.g., 40W) and the length may be at least five times greater than the height (e.g., 40H), and the width (e.g., 50W or 70W) dimension of the connection may be no greater than three times the width (e.g., 40W) of either of the beams (e.g., 40) that the connection is in between, as another example. Further, in some such embodiments, the at least one first connection and the at least one second connection are spaced apart along the length (e.g., 40L) of the beam by a distance of at least four times the width (e.g., 40W) of the beam with no other connections therebetween. Examples are shown in the drawings.

Figure 21:
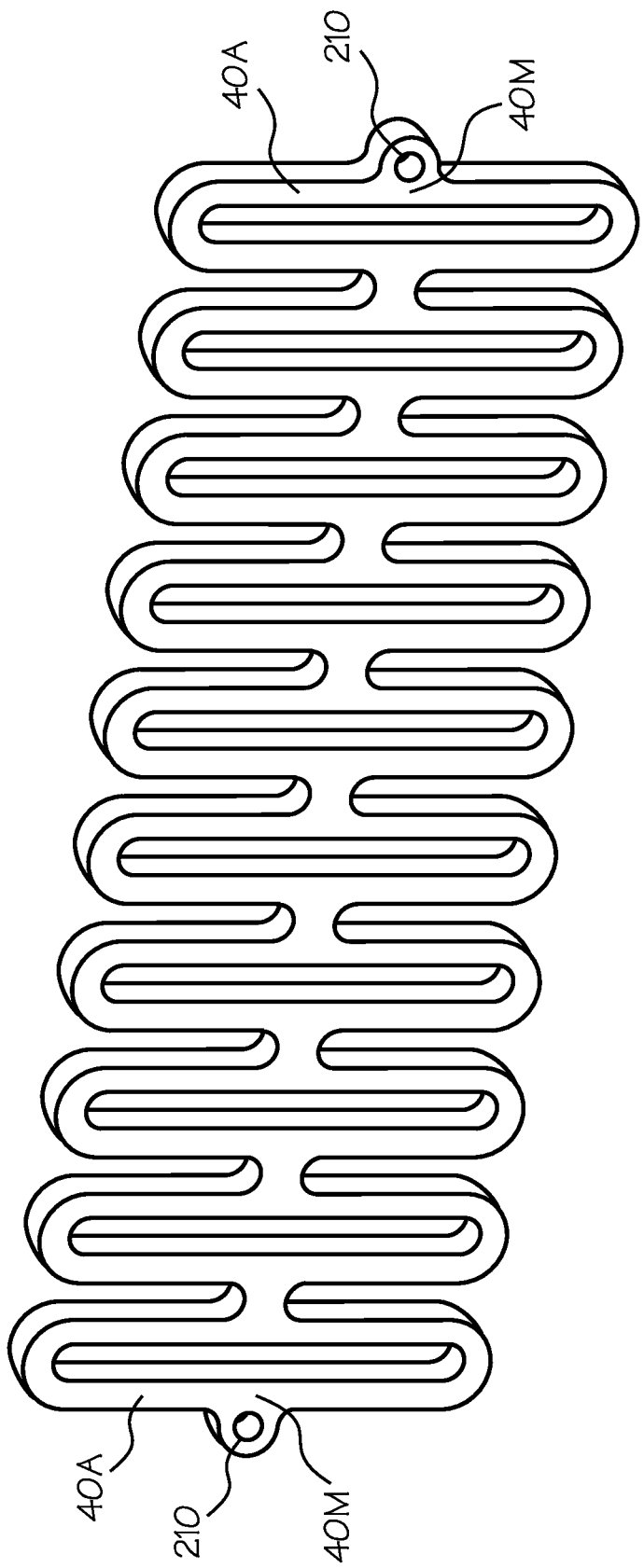
FIG. 21 is an isometric view of an apparatus that has an attachment feature at a midpoint of each end beam.
Figure 22:
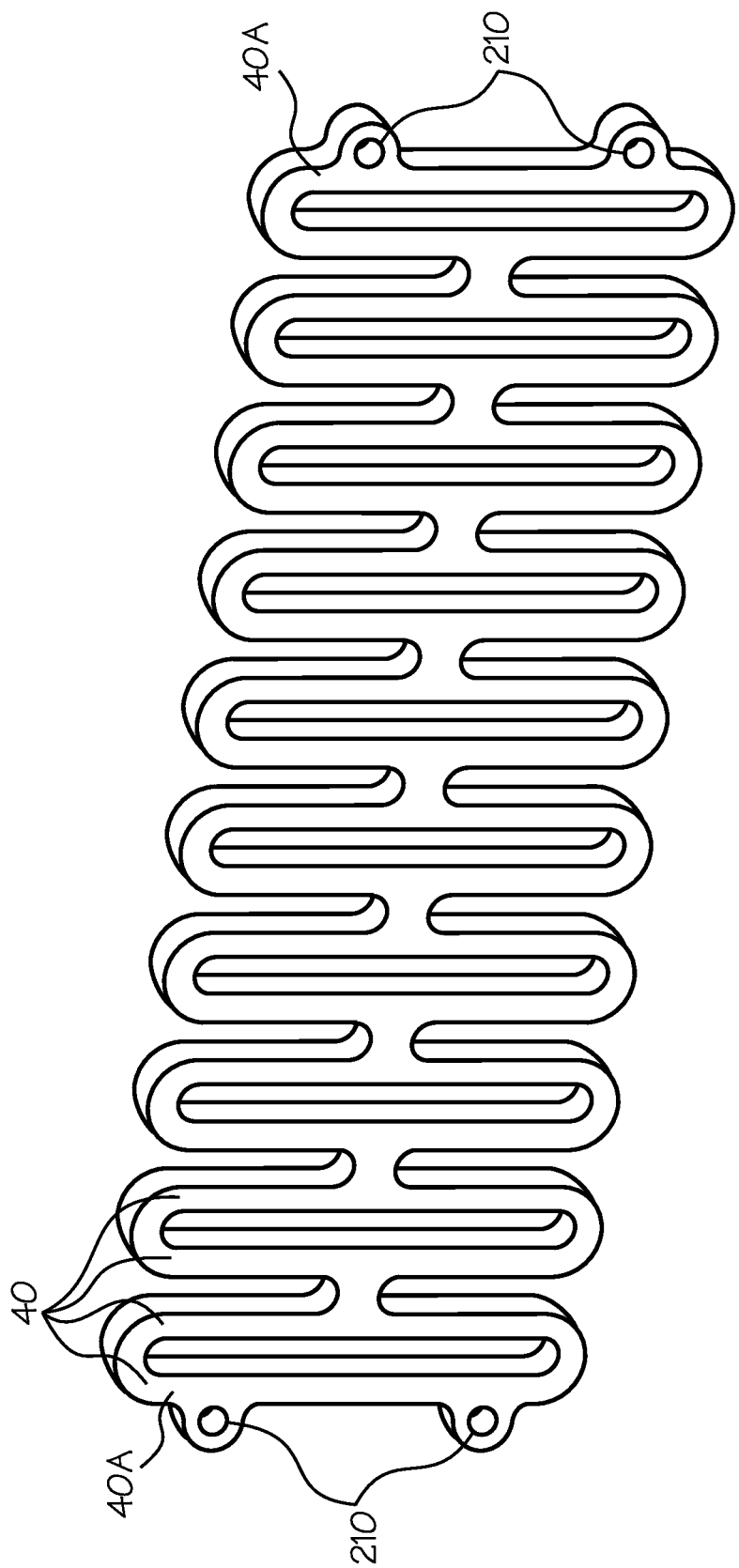
FIG. 22 is an isometric view of an apparatus that has two attachment features at each end beam.
Figure 23:
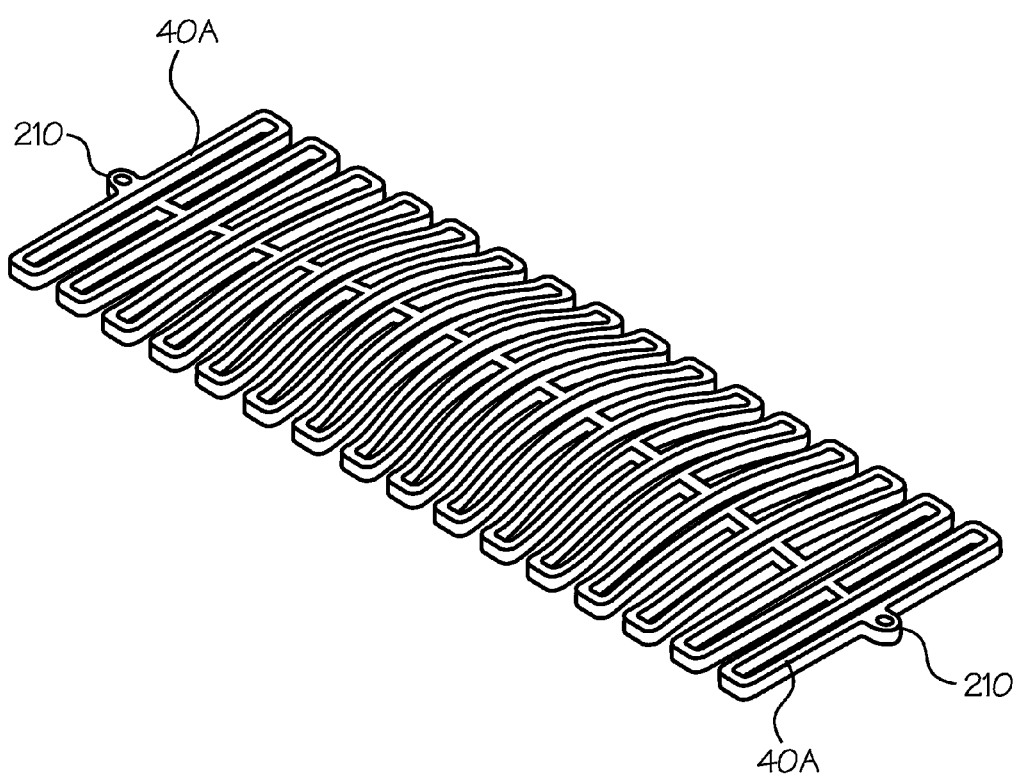
FIG. 23 is an isometric view of a flexible structural apparatus which has an attachment feature at the midpoint of each end beam and that has camber in the beams.

In certain embodiments, the flexible structural apparatus may be used as a spring, as another example. Some such embodiments may include at least one attachment feature (e.g., 210 shown in FIGS. 21-23) which may be located at an end beam (e.g., 40A), for example. A number of embodiments may include at least two or precisely two attachment features (e.g., 210), for instance, which may be located at each of the two end beams (e.g., 40A) (e.g., at opposite ends of the apparatus), for example (e.g., as shown in FIG. 22). In some embodiments, each end beam (e.g., 40a) has a midpoint (e.g., 40M) and at least one attachment feature (e.g., 210) is located at the midpoint (e.g., 40M) of an end beam (e.g., 40A). Examples are shown in FIGS. 21 and 23. In particular embodiments, the two attachment features (e.g., 210) are each located at the midpoint (e.g., 40M) of an end beam (e.g., 40A) at each of the two end beams, for example (e.g., as shown in FIGS. 21 and 23).

On the other hand, in some embodiments, the at least one attachment feature (e.g., 210) may include at least four or precisely four attachment features (e.g., as shown in FIG. 22). In some such embodiments, the four attachment features are located at the two end beams (e.g., 40A). For instance, two of the four attachment features (e.g., 210) may be located at each of the end beams (e.g., as shown in FIG. 22). Such attachment features (e.g., 210) may be at the ends (e.g., 40X and 40Y) of the end beams (e.g., 40A) or may be substantially equal distant from each of the ends (e.g., 40X and 40Y) or from the midpoints (e.g., 40M), as examples. Other embodiments may have one attachment feature in one end beam and two attachment features in the other end beam, as another example. Still other embodiments may clamp to or otherwise attach to the end beams (e.g., at one or both ends), or may push against the end beams, as other examples.

In a number of embodiments that include one or more attachment features (e.g., 210), the at least one attachment feature, for instance, may include a through hole, or each of the attachment features may include a through hole, as examples. The hole may receive a fastener or a pin, as examples. Examples of attachment features having through holes are shown in FIGS. 21-23, for example. Other examples of attachment features include slots, tabs, hooks, holes that do not extend completely through, threaded holes, and the like. The holes shown are round. Other embodiments may have holes that are square, rectangular, pentagonal, hexagonal, octagonal, triangular, slotted, splined, etc., as examples.

Various embodiments of springs may be used as tension or compression springs, as examples. Springs with at least two attachment features (e.g., 210 as shown in FIG. 22) on at least one end may be used to provide a component of spring force or movement parallel to the beams (e.g., 40), as another example. In some embodiments, springs may be located or guided between two surfaces which may be flat or curved surfaces, as examples. In some embodiments, springs may be flat (e.g., as shown in FIGS. 21 and 22, while in other embodiments, springs may be curved (e.g., have camber as described herein) for example, as shown in FIG. 23. Such curvature or camber may be the same for each of the beams (e.g., 40) in the apparatus (e.g., as shown in FIGS. 2 and 5) or may vary (e.g., as shown in FIG. 23), for example. In some embodiments, the beams (e.g., 40) may be used as leaf springs, as another example, for instance, in compression between two flat plates using the camber of the beams, or loaded at the midpoint (e.g., 40M) and ends (e.g., 40X and 40Y) of the beams, for instance. Embodiments that are used for springs may be metal or carbon fiber, as examples. Metal embodiments may be stamped or machined, as examples, and may be stainless steel (e.g., austenitic or martensitic) or carbon steel, for instance. Some embodiments may be work hardened or heat treated, as examples.

Certain embodiments include a base (e.g., 240 or 250) and a removable top portion (e.g., 241). As used herein, "removable" means that the parts can be disassembled from each other in whole or in part (e.g., swung away on a hinge, such as hinge 244) without significant damage to either part (e.g., 240 or 241) and reassembled in the same manner multiple times. In some wound covering devices, for example, a base (e.g., 240 or 250) may remain on the patient's body while a removable top portion (e.g., 241, for instance, comprising beams 40 and connections 50, 70, or both) may be removed (or swung out of the way on hinge 244) for inspection or treatment of the wound, for instance. In some embodiments, the base (e.g., 240 or 250) may be flexible (e.g., made of foam or an elastomer, as examples).

As illustrated in FIGS. 24 and 25, some specific embodiments may include a ring pad (e.g., 240 or 250) wherein the beams, the connections, the lateral support members, the coupling members, the end beams, or a combination thereof, for example, are configured to mount on the ring pad. In some embodiments, the ring pad may be made of or include foam, for example, and may be relatively flexible. Further, in a number of embodiments, the ring pad may include one split (e.g., 255) or may include at least two splits (e.g., 255) and may consist of multiple segments (e.g., 257). The embodiment of the ring pad shown in FIG. 25, for example, has precisely two splits 255 and the ring pad 250 consists of precisely two segments 257. Other embodiments of ring pads may have one, three, four, five, six, or more splits, and may consist of only one segment, three segments, four segments, five segments, six segments, or more segments, as examples. In other embodiments, the ring pad may be a continuous ring with no splits, as another example (e.g., as shown in FIG. 24. In different embodiments, the ring pad may be oval (e.g., as shown in FIGS. 24 and 25) or may be round, square, rectangular, hexagonal, octagonal, triangular, or rhomboidal, as examples. Some embodiments with straight sides may have rounded corners, as other examples.

In various embodiments, the ring pad may include a substantially flat bottom surface, a substantially flat top surface, or both, for example. Further, in some embodiments, the ring pad may include an adhesive (e.g., similar to 130) that is applied to at least a portion of the bottom surface, an adhesive that is applied to at least a portion of the top surface, or both. For example, in particular embodiments, the adhesive may be applied to all or essentially all of the bottom surface, to all or essentially all of the top surface, or both. In wound covering embodiments, the adhesive on the bottom surface may be used to attach the ring pad to the patient's skin, for instance. Further, in various embodiments, the adhesive on the top surface may be used to attach the beams, connections, end beams, or the like, to the ring pad, for example. In some embodiments, a reusable adhesive may be used. Other embodiments may employ a ring pad fastener (e.g., 246) instead of or in addition to the adhesive on the top surface, for example.

In various embodiments, a ring pad fastener (e.g., 246) may be configured to attach the ring pad (e.g., 240) to the beams (e.g., the end beams 40A), the connections (e.g., 50), the lateral support members, the coupling members, or a combination thereof, for example. In some embodiments, for instance, the ring pad fastener may include, or the top surface of the ring pad may include, a hook and loop fastener (e.g., Velcro) that may include multiple hooks and multiple loops, for instance. For example, the top surface of the ring pad (e.g., 240 or 250) may be covered with loops at the bottom surface of the connections (e.g., 50) or ends (e.g., 40X and 40Y) of the beams, the bottom surface of the end beams (e.g., 40A), or both, may be covered (e.g., in whole or in part) with hooks sized and shaped to attach to the loops. In a number of embodiments, the beams and connections (e.g., top portion 241) may be removable from the ring pad (e.g., for inspection or treatment of the wound) and may be configured to be reattached without significant damage to the apparatus or fastener, for instance.

In some embodiments, the at least one ring pad fastener may include at least one snap fastener, as another example. The embodiment shown in FIG. 24 has one snap fastener 246 and one hinge 244, but other embodiments may have multiple snap fasteners such as two, three, four, five, six, seven, eight, ten, or more snap fasters, as other examples, with or without one or more hinges. In some embodiments, snap fasteners (e.g., 246) may attach to or be part of one or both end beams (e.g., 40A), to connections (e.g., 50) at the ends of beams, or a combination thereof, as examples. In certain embodiments, a hinge (or multiple hinges) (e.g., 244) may be used or configured to attach the ring pad (e.g., 240) to one or more of the beams (e.g., an end beam 40A), the connections (e.g., 50), the lateral support members, the coupling members, or a combination thereof, as examples.

Figure 26:
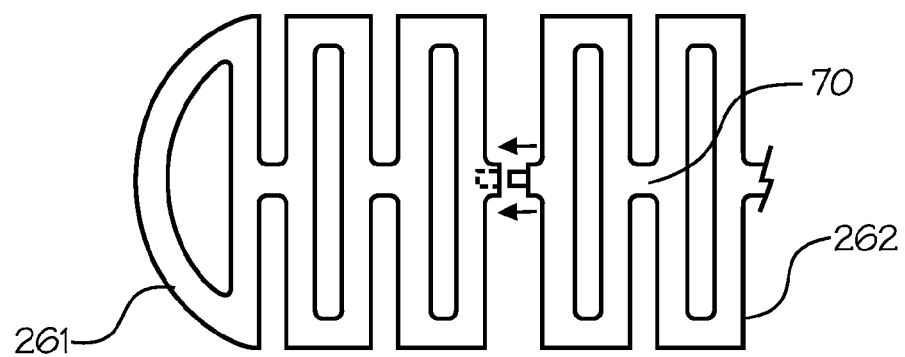
FIG. 26 is a multiple view drawing that includes a top view, an isometric view, and some cross-sectional detail views of a flexible structural apparatus which has a module fastener located in a connection at the middle of particular beams.
Figure 26:
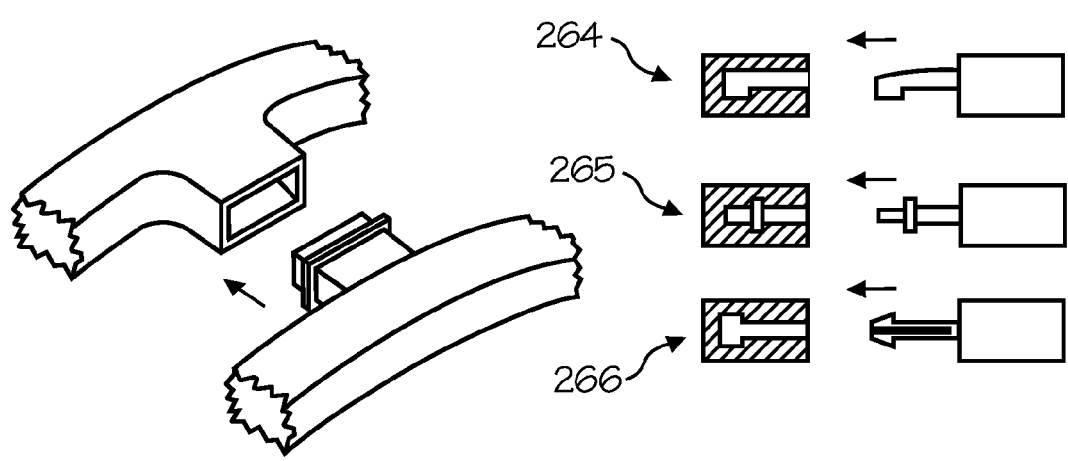
Figure 27:
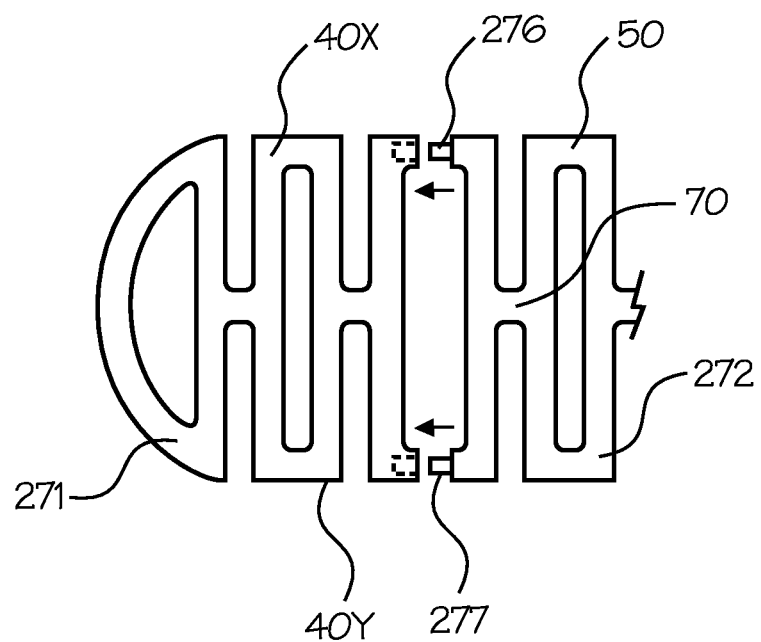
FIG. 27 is a multiple view drawing that includes a top view and an isometric view of another embodiment of a flexible structural apparatus which has module fasteners located in connections at the ends of certain beams.
Figure 27:
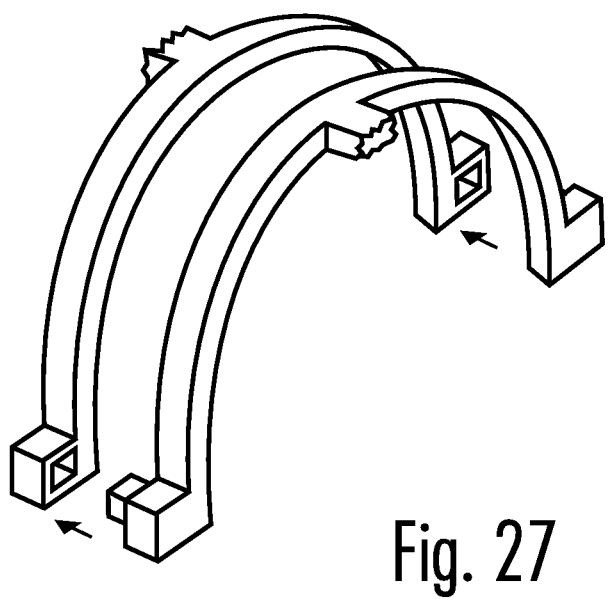

Many embodiments (e.g., of wound covering devices) may be made long (e.g., have more intermediate beams 40B than may be needed or desirable in many applications) and may be cut to length (e.g., to fit the size of the wound). Other embodiments may be shorter (e.g., have fewer intermediate beams 40B) and may be connected together to be used with larger wounds. For example, in a number of embodiments, the flexible structural apparatus or the wound covering may include at least one module fastener (e.g., 264, 265, or 266 shown in FIG. 26) configured to connect multiple modules (e.g., 261 and 262) of the flexible structural apparatus or the wound covering together to form a larger flexible structural apparatus or wound covering, for example. FIGS. 26 and 27 illustrate examples of such embodiments. In the application of wound covering devices, pieces of the device (e.g., modules 261 and 262 or 271 and 272) can be connected together to fit the size of the wound, for instance. As illustrated, in some embodiments, the (e.g., at least one) module fastener (e.g., 264, 265, or 266) is located in at least one of the connections (e.g., 50 or 70) or in at least one of the coupling members, for example. In some embodiments, the (e.g., at least one) module fastener is located in at least one of the end beams (e.g., 40A) of the module or in at least one of the lateral support members, for example.

The (e.g., at least one) module fastener (e.g., 264, 265, or 266) may be a snap fastener, for example. Certain alternate embodiments of module fasteners are shown in the detail cross-section views of FIG. 26, for example. In some embodiments, the at least one module fastener (e.g., 264, 265, or 266) is located in at least one of the first connections (e.g., 50, shown in FIG. 27) described herein, while in other embodiments, the at least one module fastener is located in at least one of the second connections (e.g., 70, shown in FIG. 26). Still other embodiments may have module fasteners in both first and second connections, as another example. In some embodiments, the at least one module fastener is located proximate a middle (e.g., 40M) of a beam (e.g., an end beam of the module), and in some embodiments, the at least one module fastener may include a first module fastener 276 and a second module fastener 277 and the first module fastener and the second module fastener may be located at opposite ends (e.g., 40X and 40Y) of a beam (e.g., an end beam of the module), for instance. Moreover, in some embodiments, where various fasteners are described herein, tape may be used instead of, or in addition to, other fasteners. Sticky or non-sticky (e.g., Coban) tape may be used, in various embodiments, for instance.

When viewed from above, various embodiments may have a rectangular shape which may have plain or square ends (e.g., as shown in FIGS. 3, 4, 6, 15, 17, 21, 22, and 23) or may have jagged ends (e.g., as shown in FIGS. 10 and 11). Some embodiments may have rounded corners or rounded ends (e.g., FIGS. 13, 15, 21, 22, 23, 26 and 27) or may be oval (e.g., FIGS. 7, 14, 24, and 25) or round in shape, as other examples. Other embodiments may be triangular, pentagonal, hexagonal, octagonal, rhombic, crescent shaped, shaped like a half moon or a gibbous moon, or shaped like a "C", a "J", an "L", an "S", a "T", a "U", a "V", an "X", a "Y", or a "Z", as examples, or other shapes when viewed from above. For instance, an "L" shaped wound covering device may be used to cover an "L" shaped stitched cut. Some embodiments may have a shape or part of such a shape or a combination of such shapes (e.g., a combination of rectangles). FIGS. 8 and 9 illustrate examples of particular other shapes when viewed from above. In some embodiments, various such shapes, or other shapes, can be formed from modular components (e.g., of FIG. 26 or 27).

Other embodiments include various methods of use and various method of manufacture of such flexible structural apparatuses, springs, and wound covering devices. Methods in accordance with the invention include various combinations of the acts described herein, which may be combined with acts of forming, obtaining, or providing apparatuses or parts with various aspects of the structure described herein, as examples.

What is claimed is:

1. A flexible structural apparatus comprising:
    multiple substantially parallel beams comprising two end beams and multiple intermediate beams, wherein the multiple intermediate beams are in between the two end beams, each of the multiple substantially parallel beams having a beam length, a beam width, and a beam height, wherein, for a plurality of the multiple substantially parallel beams, the beam length is at least four times greater than the beam width and the beam length is at least four times greater than the beam height;
    multiple connections between the multiple substantially parallel beams, wherein each of the multiple connections connects one of the multiple substantially parallel beams to one other of the multiple substantially parallel beams, wherein each of the multiple substantially parallel beams has at least one of the multiple connections to at least one other of the multiple substantially parallel beams and each of the multiple intermediate beams has a plurality of the multiple connections to at least two other of the multiple substantially parallel beams, wherein each of the multiple connections has a connection width dimension parallel to the beam length, wherein the connection width dimension of each of the multiple connections is no greater than one fourth of the beam length of either of the multiple substantially parallel beams that the connection width dimension is between, wherein each of the multiple intermediate beams is restrained relative to other of the multiple substantially parallel beams only at the multiple connections; and
    wherein the multiple connections consist of multiple first connections and multiple second connections wherein a plurality of the multiple intermediate beams each have precisely two of the multiple first connections to precisely one first adjacent beam of the multiple substantially parallel beams and precisely one of the multiple second connections to precisely one second adjacent beam of the multiple substantially parallel beams, wherein for each of the plurality of the multiple intermediate beams, the precisely two multiple first connections and the precisely one of the multiple second connections are spaced apart along the beam length by a first distance of at least one fourth of the beam length with no other of the multiple connections therebetween, and wherein, from one of the two end beams to an other of the two end beams, the multiple connections alternate between the precisely two of the multiple first connections and the precisely one of the multiple second connections.

2. The flexible structural apparatus of claim 1 wherein a plurality of the multiple intermediate beams each have a preformed camber in a direction of the beam height.

3. The flexible structural apparatus of claim 2 wherein different of the multiple intermediate beams have a different amount of the preformed camber in the direction of the beam height, wherein the amount of the preformed camber varies between the multiple intermediate beams from a lesser amount of the preformed camber near the two end beams to a greater amount of the preformed camber midway between the two end beams.

4. The flexible structural apparatus of claim 1 wherein each of the multiple substantially parallel beams has a first end and a second end, and wherein, for each of the multiple intermediate beams, one of the multiple first connections is located along the beam length within a second distance of no more than one fifth of the beam length from the first end and one of the multiple first connections is located along the beam length within a third distance of no more than one fifth of the beam length from the second end.

5. The flexible structural apparatus of claim 1 wherein each of the multiple substantially parallel beams has a midpoint, and wherein, for each of the multiple intermediate beams, the precisely one of the multiple second connections is located along the beam length within a fourth distance of no more than one fifth of the beam length from the midpoint.

6. The flexible structural apparatus of claim 1 wherein different of the multiple intermediate beams have a different beam length, wherein the different beam lengths varies between the multiple intermediate beams from a lesser beam length near the two end beams to a greater beam length midway between the two end beams.

7. The flexible structural apparatus of claim 1 wherein each of the multiple substantially parallel beams has a first end and a second end, and wherein, for each of a plurality of the multiple substantially parallel beams, at least the first end and the second end comprise an adhesive.

8. The flexible structural apparatus of claim 1 further comprising a layer that extends across at least a portion of a plurality of the multiple substantially parallel beams, wherein each of the plurality of the multiple substantially parallel beams has a first end and a second end, and wherein, for each of the plurality of the multiple substantially parallel beams, the layer extends at least from the first end to the second end, and wherein the layer extends across each of the multiple substantially parallel beams of the apparatus.

9. The flexible structural apparatus of claim 1 wherein the multiple substantially parallel beams and the multiple connections are all formed from a common piece of material.

10. The flexible structural apparatus of claim 1 wherein a plurality of the multiple substantially parallel beams each have multiple bends.

11. The flexible structural apparatus of claim 1 wherein the multiple connections between the multiple intermediate beams each have a connection length perpendicular to the beam length and parallel to the beam width, wherein, for a plurality of the multiple connections, the connection length is less than one fifth of the beam length that the connection length is in between.

12. The flexible structural apparatus of claim 1 wherein the multiple connections between the multiple intermediate beams each have a connection length perpendicular to the beam length of the multiple intermediate beams and parallel to the beam width of the multiple intermediate beams, wherein, for a plurality of the multiple connections, the connection length is greater than the beam width of the multiple intermediate beams that the connection length is in between.

13. The flexible structural apparatus of claim 1 wherein the multiple connections between the multiple intermediate beams each have a connection length perpendicular to the beam length and parallel to the beam width, wherein the multiple connections each have a connection width perpendicular to the beam width and parallel to the beam length, wherein, for a plurality of the multiple connections, the connection length is greater than the connection width.

14. The flexible structural apparatus of claim 1 wherein the multiple connections between the multiple intermediate beams each have a connection length perpendicular to the beam length and parallel to the beam width, wherein the multiple connections each have a connection width perpendicular to the beam width and parallel to the beam length, wherein, for a plurality of the multiple connections, the connection length is less than twice the connection width.

15. The flexible structural apparatus of claim 1 wherein for each of the multiple intermediate beams, the precisely two first connections and the precisely one second connection are spaced apart along the beam length by a fifth distance of at least four times the beam width.

16. A flexible structural apparatus comprising:
multiple substantially parallel beams comprising two end beams and multiple intermediate beams, wherein the multiple intermediate beams are in between the two end beams, each of the multiple substantially parallel beams having a beam length, a beam width, and a beam height, wherein, for a plurality of the multiple substantially parallel beams, the beam length is at least four times greater than the beam width and the beam length is at least five times greater than the beam height;
multiple connections between the multiple substantially parallel beams, wherein each of the multiple connections connects one of the multiple substantially parallel beams to one other of the multiple substantially parallel beams, wherein each of the multiple substantially parallel beams has at least one of the multiple connections to at least one other of the multiple substantially parallel beams and each of the multiple intermediate beams has a plurality of the multiple connections to two other of the multiple substantially parallel beams, wherein each of the plurality of the multiple connections has a connection width dimension parallel to the beam length, wherein the connection width dimension is no greater than three times the beam width of either of the multiple substantially parallel beams that the connection width dimension is between; and wherein each of the multiple intermediate beams is restrained relative to other of the multiple substantially parallel beams only at the multiple connections; and
wherein the multiple connections consist of multiple first connections and multiple second connections wherein a plurality of the multiple intermediate beams each have at least one first connection to precisely one first adjacent of the multiple substantially parallel beams and at least one second connection to precisely one second adjacent of the multiple substantially parallel beams, wherein for each of the multiple intermediate beams, the at least one first connection and the at least one second connection are spaced apart along the beam length by a first distance of at least four times the beam width with no other of the multiple connections therebetween, wherein, from one of the two end beams to an other of the two end beams, the multiple connections alternate between the at least one first connection and the at least one second connection.

17. The flexible structural apparatus of claim 16 further comprising at least two attachment features wherein the two attachment features are located at each of the two end beams.

18. The flexible structural apparatus of claim 17 wherein at least one attachment feature comprises a through hole.

19. The flexible structural apparatus of claim 16 wherein the apparatus is used as a spring.

20. The flexible structural apparatus of claim 16 wherein the multiple intermediate beams each have precisely two first connections to the precisely one first adjacent of the multiple substantially parallel beams and precisely one second connection to the precisely one second adjacent of the multiple substantially parallel beams and wherein, from the one of the two end beams to the other of the two end beams, the multiple connections alternate between the precisely two first connections and the precisely one second connection.

* * * * *